(12) United States Patent
Duffill et al.

(10) Patent No.: US 7,908,097 B2
(45) Date of Patent: Mar. 15, 2011

(54) METHODS AND METER ELECTRONICS FOR RAPIDLY DETECTING A NON-UNIFORMITY OF A MATERIAL FLOWING THROUGH A CORIOLIS FLOWMETER

(75) Inventors: Graeme Ralph Duffill, Scottsdale, AZ (US); Mark James Bell, Arvada, CO (US); Craig B. McAnally, Thornton, CO (US); Richard L. Maginnis, Lafayette, CO (US)

(73) Assignee: Micro Motion, Inc., Boulder, CO (US)

( * ) Notice: Subject to any disclaimer, the term of this patent is extended or adjusted under 35 U.S.C. 154(b) by 245 days.

(21) Appl. No.: 11/914,819

(22) PCT Filed: May 24, 2006

(86) PCT No.: PCT/US2006/020188
§ 371 (c)(1),
(2), (4) Date: Nov. 19, 2007

(87) PCT Pub. No.: WO2006/130415
PCT Pub. Date: Dec. 7, 2006

(65) Prior Publication Data
US 2008/0189067 A1    Aug. 7, 2008

Related U.S. Application Data

(60) Provisional application No. 60/685,739, filed on May 27, 2005.

(51) Int. Cl.
*G06F 19/00* (2006.01)
*G01F 1/84* (2006.01)

(52) U.S. Cl. ..................... 702/45; 73/861.356

(58) Field of Classification Search .................... 702/45, 702/100, 51, 56; 73/861.354–861.355, 861.356
See application file for complete search history.

(56) References Cited

U.S. PATENT DOCUMENTS

| 3,750,034 | A |   | 7/1973 | Marucci et al. |
|---|---|---|---|---|
| 4,607,520 | A | * | 8/1986 | Dam .......................... 73/19.03 |
| 5,578,764 | A | * | 11/1996 | Yokoi et al. .............. 73/861.356 |
| 5,594,180 | A | * | 1/1997 | Carpenter et al. ........ 73/861.356 |
| 6,092,409 | A |   | 7/2000 | Patten et al. |
| 6,327,914 | B1 | * | 12/2001 | Dutton ..................... 73/861.356 |
| 6,505,131 | B1 | * | 1/2003 | Henrot ........................... 702/54 |
| 6,505,519 | B2 |   | 1/2003 | Henry et al. |
| 2004/0123645 | A1 |   | 7/2004 | Storm et al. |

FOREIGN PATENT DOCUMENTS

| GB | 2418084 B | * | 1/2010 |
|---|---|---|---|
| JP | 07-181069 |   | 7/1995 |
| WO | WO/2006/071454 A1 |   | 7/2006 |

* cited by examiner

*Primary Examiner* — Bryan Bui
(74) *Attorney, Agent, or Firm* — The Ollila Law Group LLC

(57) ABSTRACT

Meter electronics (20) and methods for detecting a flow anomaly in a flow material flowing through a flow meter (5) are provided. The meter electronics (20) includes an interface (201) for receiving a vibrational response of the flow material, with the vibrational response including at least a first sensor signal and a second sensor signal, and a processing system (203) in communication with the interface (201). The processing system (203) is configured to receive the vibrational response from the interface (201), generate a ninety degree phase shift from the first sensor signal and generate at least one flow characteristic using at least the first sensor signal and the ninety degree phase shift, compare the at least one flow characteristic to at least one anomaly profile, detect a shift in the vibrational response if the at least one flow characteristic falls within the anomaly profile, and indicate an anomaly condition as a result of the detecting.

42 Claims, 17 Drawing Sheets

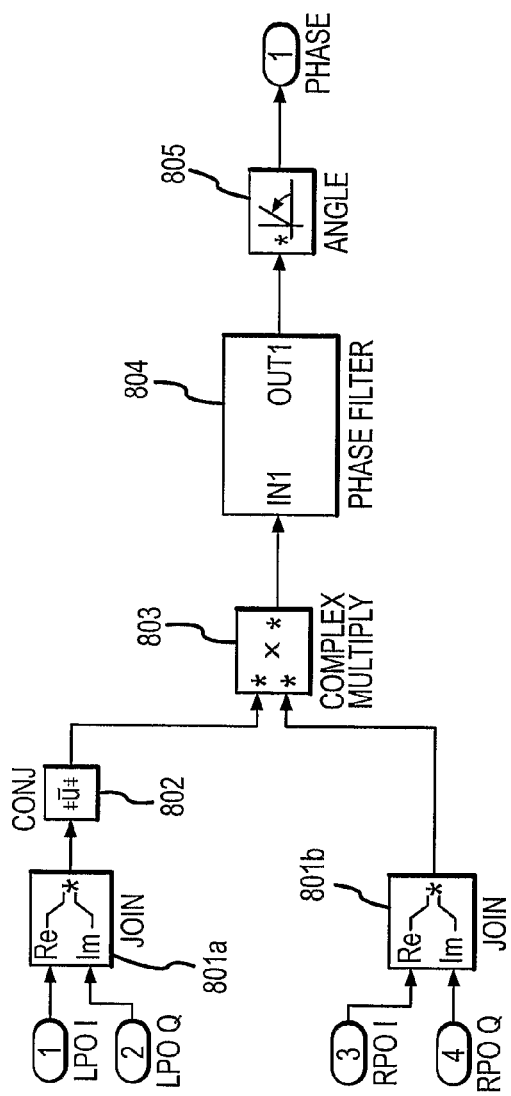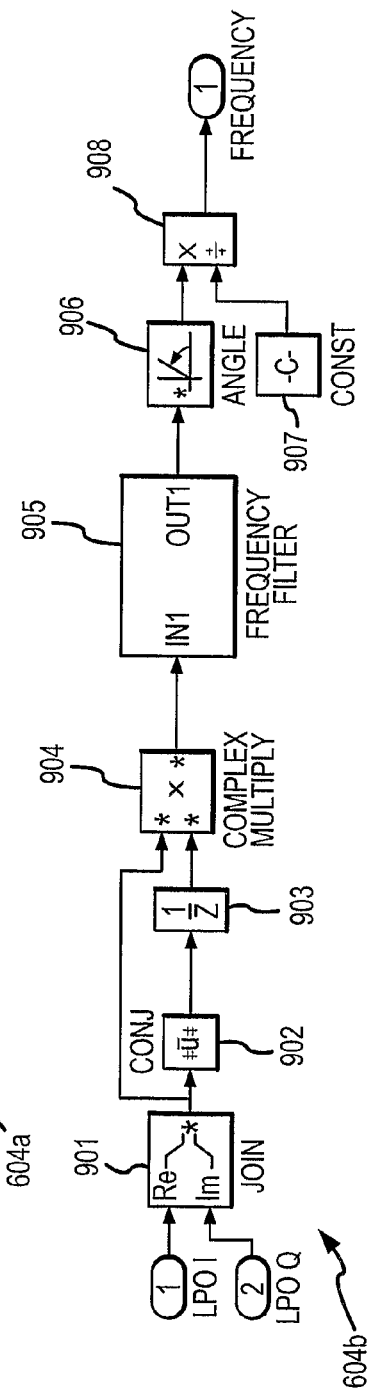
FIG. 8
FIG. 9

METHODS AND METER ELECTRONICS FOR RAPIDLY DETECTING A NON-UNIFORMITY OF A MATERIAL FLOWING THROUGH A CORIOLIS FLOWMETER

The present application claims the benefit of U.S. Provisional Patent Application No. 60/685,739, entitled "Meter Electronics and Methods for Detecting a Flow Anomaly in a Flow Material", filed on May 27, 2005.

BACKGROUND OF THE INVENTION

1. Field of the Invention

The present invention relates to meter electronics and methods for detecting a flow anomaly in a flow material flowing through a flow meter.

2. Statement of the Problem

It is known to use Coriolis mass flow meters to measure mass flow and other information of materials flowing through a pipeline as disclosed in U.S. Pat. No. 4,491,025 issued to J. E. Smith, et al. of Jan. 1, 1985 and Re. 31,450 to J. E. Smith of Feb. 11, 1982. These flow meters have one or more flow tubes of different configurations. Each conduit configuration may be viewed as having a set of natural vibration modes including, for example, simple bending, torsional, radial and coupled modes. In a typical Coriolis mass flow measurement application, a conduit configuration is excited in one or more vibration modes as a material flows through the conduit, and motion of the conduit is measured at points spaced along the conduit.

The vibrational modes of the material filled systems are defined in part by the combined mass of the flow tubes and the material within the flow tubes. Material flows into the flow meter from a connected pipeline on the inlet side of the flow meter. The material is then directed through the flow tube or flow tubes and exits the flow meter to a pipeline connected on the outlet side.

A driver applies a force to the flow tube. The force causes the flow tube to oscillate. When there is no material flowing through the flow meter, all points along a flow tube oscillate with an identical phase. As a material begins to flow through the flow tube, Coriolis accelerations cause each point along the flow tube to have a different phase with respect to other points along the flow tube. The phase on the inlet side of the flow tube lags the driver, while the phase on the outlet side leads the driver. Sensors are placed at different points on the flow tube to produce sinusoidal signals representative of the motion of the flow tube at the different points. The phase difference between the two sensor signals is proportional to the mass flow rate of the material flowing through the flow tube or flow tubes. In one prior art approach either a Discrete Fourier Transform (DFT) or a Fast Fourier Transform (FFT) is used to determine the phase difference between the sensor signals. The phase difference and a vibrational frequency response of the flow tube assembly are used to obtain the mass flow rate.

In one prior art approach, an independent reference signal is used to determine a pickoff signal frequency, such as by using the frequency sent to the vibrational driver system. In another prior art approach, the vibrational response frequency generated by a pickoff sensor can be determined by centering to that frequency in a notch filter, wherein the prior art flowmeter attempts to keep the notch of the notch filter at the pickoff sensor frequency. This prior art technique works fairly well under quiescent conditions, where the flow material in the flowmeter is uniform and where the resulting pickoff signal frequency is relatively stable. However, the phase measurement of the prior art suffers when the flow material is not uniform, such as in two-phase flows where the flow material comprises a liquid and a solid or where there are air bubbles in the liquid flow material. In such situations, the prior art determined frequency can fluctuate rapidly. During conditions of fast and large frequency transitions, it is possible for the pickoff signals to move outside the filter bandwidth, yielding incorrect phase and frequency measurements. This also is a problem in empty-full-empty batching, where the flow meter is repeatedly operated in alternating empty and full conditions. Also, if the frequency of the sensor moves rapidly, a demodulation process will not be able to keep up with the actual or measured frequency, causing demodulation at an incorrect frequency. It should be understood that if the determined frequency is incorrect or inaccurate, then subsequently derived values of density, volume flow rate, etc., will also be incorrect and inaccurate. Moreover, the error can be compounded in subsequent flow characteristic determinations.

In the prior art, the pickoff signals can be digitized and digitally manipulated in order to implement the notch filter. The notch filter accepts only a narrow band of frequencies. Therefore, when the target frequency is changing, the notch filter may not be able to track the target signal for a period of time. Typically, the digital notch filter implementation takes 1-2 seconds to track to the fluctuating target signal. Due to the time required by the prior art to determine the frequency, the result is not only that the frequency and phase determinations contain errors, but also that the error measurement encompasses a time span that exceeds the time span during which the error and/or two-phase flow actually occur. This is due to the relative slowness of response of a notch filter implementation.

The result is that the prior art flowmeter cannot accurately, quickly, or satisfactorily track or determine a pickoff sensor frequency during two-phase flow of the flow material in the flowmeter. Consequently, the phase determination is likewise slow and error prone, as the prior art derives the phase difference using the determined pickoff frequency. Therefore, any error in the frequency determination is compounded in the phase determination. The result is increased error in the frequency determination and in the phase determination, leading to increased error in determining the mass flow rate. In addition, because the determined frequency value is used to determine a density value (density is approximately equal to one over frequency squared), an error in the frequency determination is repeated or compounded in the density determination. This is also true for a determination of volume flow rate, where the volume flow rate is equal to mass flow rate divided by density.

In many flow applications, it is possible to have anomalies entrained in the flow material. A multi-phase flow typically includes multiple materials in a flow. The multiple materials can be desirable or undesirable, including unwanted materials or portions (i.e., anomalies) in the flow material. It would be advantageous if desirable and/or undesirable anomalies could be detected and quantified in the flow material. Anomaly detection could make possible the effective removal or prevention of such anomalies or could make possible a desired level of anomalies.

An anomaly can comprise gas bubbles or air bubbles entrained in the flow material. Examples are air bubbles in water or natural gas bubbles in an oil well output. An anomaly can comprise a foreign liquid in the flow material. For example, water can exists in crude oil in an oil well output. An anomaly can comprise a solid in the flow material. For example, the flow material can include pieces of metal that have broken or flaked off from pipes, pumps, valves, etc., in a fluid processing facility. It should be understood that anomalies in the flow material can include combinations of the gas, liquid, and solid anomalies discussed above.

The anomalies can cause erroneous mass flow rates in a flow meter, among other things. It is highly desirable that a flow meter accurately measure a mass flow rate of the flow liquid even in the presence of anomalies in the flow liquid.

SUMMARY OF THE SOLUTION

The above and other problems are solved and an advance in the art is achieved through the provision of meter electronics and methods for detecting a flow anomaly in a flow material.

Meter electronics for detecting a flow anomaly in a flow material flowing through a flow meter is provided according to an embodiment of the invention. The meter electronics comprises an interface for receiving a vibrational response of the flow material, with the vibrational response including at least a first sensor signal and a second sensor signal, and a processing system in communication with the interface. The processing system is configured to receive the vibrational response from the interface and generate a ninety degree phase shift from the first sensor signal and generate at least one flow characteristic using at least the first sensor signal and the ninety degree phase shift. The processing system is further configured to compare the at least one flow characteristic to at least one anomaly profile, detect a shift in the vibrational response if the at least one flow characteristic falls within the anomaly profile, and indicate an anomaly condition as a result of the detecting.

A method for detecting a flow anomaly in a flow material flowing through a flow meter is provided according to an embodiment of the invention. The method comprises receiving a vibrational response from the flow meter. The vibrational response includes at least a first sensor signal and a second sensor signal. The method further comprises generating a ninety degree phase shift from the first sensor signal and generating at least one flow characteristic using at least the first sensor signal and the ninety degree phase shift. The method further comprises comparing the at least one flow characteristic to at least one anomaly profile, detecting a shift in the vibrational response if the at least one flow characteristic falls within the anomaly profile, and indicating an anomaly condition as a result of the detecting.

A method for detecting a flow anomaly in a flow material flowing through a flow meter is provided according to an embodiment of the invention. The method comprises receiving a vibrational response from the flow meter. The vibrational response includes at least a first sensor signal and a second sensor signal. The method further comprises generating a ninety degree phase shift from the first sensor signal and generating at least one flow characteristic using at least the first sensor signal and the ninety degree phase shift. The method further comprises comparing the at least one flow characteristic to at least a gas anomaly profile, detecting a shift in the vibrational response if the at least one flow characteristic falls within the gas anomaly profile, and incrementing a bubble count as a result of the detecting.

ASPECTS OF THE INVENTION

In one aspect of the meter electronics, the interface includes a digitizer configured to digitize the sensor signal.

In another aspect of the meter electronics, the processing system is further configured to iteratively perform the receiving, generating, comparing, detecting, and indicating.

In yet another aspect of the meter electronics, the flow meter comprises a Coriolis flow meter.

In yet another aspect of the meter electronics, the flow meter comprises a vibrating densitometer.

In yet another aspect of the meter electronics, the at least one flow characteristic comprises a frequency response.

In yet another aspect of the meter electronics, the at least one flow characteristic comprises a phase difference response, and wherein the processing system is further configured to compute the phase difference response using the ninety degree phase shift, the first sensor signal, and the second sensor signal.

In yet another aspect of the meter electronics, the at least one flow characteristic comprises a phase difference response, and wherein the processing system is further configured to generate a second ninety degree phase shift from the second sensor signal and compute the phase difference response using the ninety degree phase shift, the second ninety degree phase shift, the first sensor signal, and the second sensor signal.

In yet another aspect of the meter electronics, the at least one flow characteristic comprises a sensor signal time delay response.

In yet another aspect of the meter electronics, the at least one flow characteristic comprises a mass flow rate response.

In yet another aspect of the meter electronics, the at least one flow characteristic comprises a density response.

In yet another aspect of the meter electronics, the indicating comprises indicating a solids anomaly.

In yet another aspect of the meter electronics, the indicating comprises indicating a foreign liquid anomaly.

In yet another aspect of the meter electronics, the indicating comprises indicating a gas anomaly.

In yet another aspect of the meter electronics, the indicating comprises indicating an air bubble anomaly.

In yet another aspect of the meter electronics, the indicating comprises setting an anomaly alarm condition.

In yet another aspect of the meter electronics, the indicating comprises incrementing an anomaly count.

In one aspect of the method, the method further comprises iteratively performing the receiving, generating, comparing, detecting, and indicating.

In another aspect of the method, the flow meter comprises a Coriolis flow meter.

In yet another aspect of the method, the flow meter comprises a vibrating densitometer.

In yet another aspect of the method, the at least one flow characteristic further comprises a frequency response.

In yet another aspect of the method, the at least one flow characteristic further comprises a phase difference response and with the generating the at least one flow characteristic further comprising computing the phase difference response using the ninety degree phase shift, the first sensor signal, and the second sensor signal.

In yet another aspect of the method, the at least one flow characteristic further comprises a phase difference response and the generating the at least one flow characteristic further comprises generating a second ninety degree phase shift from the second sensor signal and computing the phase difference response using the ninety degree phase shift, the second ninety degree phase shift, the first sensor signal, and the second sensor signal.

In yet another aspect of the method, the at least one flow characteristic further comprises a sensor signal time delay response.

In yet another aspect of the method, the at least one flow characteristic further comprises a mass flow rate response.

In yet another aspect of the method, the at least one flow characteristic further comprises a density response.

In yet another aspect of the method, the indicating comprises indicating a solids anomaly.

In yet another aspect of the method, the indicating comprises indicating a foreign liquid anomaly.

In yet another aspect of the method, the indicating comprises indicating a gas anomaly.

In yet another aspect of the method, the indicating comprising indicating an air bubble anomaly.

In yet another aspect of the method, the indicating comprises setting an anomaly alarm condition.

In yet another aspect of the method, the indicating comprises incrementing an anomaly count.

DESCRIPTION OF THE DRAWINGS

The same reference number represents the same element on all drawings.

FIGS. 8 and 9 are block diagrams of two independent branches of the analysis block according to an embodiment of the invention.

DETAILED DESCRIPTION OF THE INVENTION

FIGS. 1-20 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
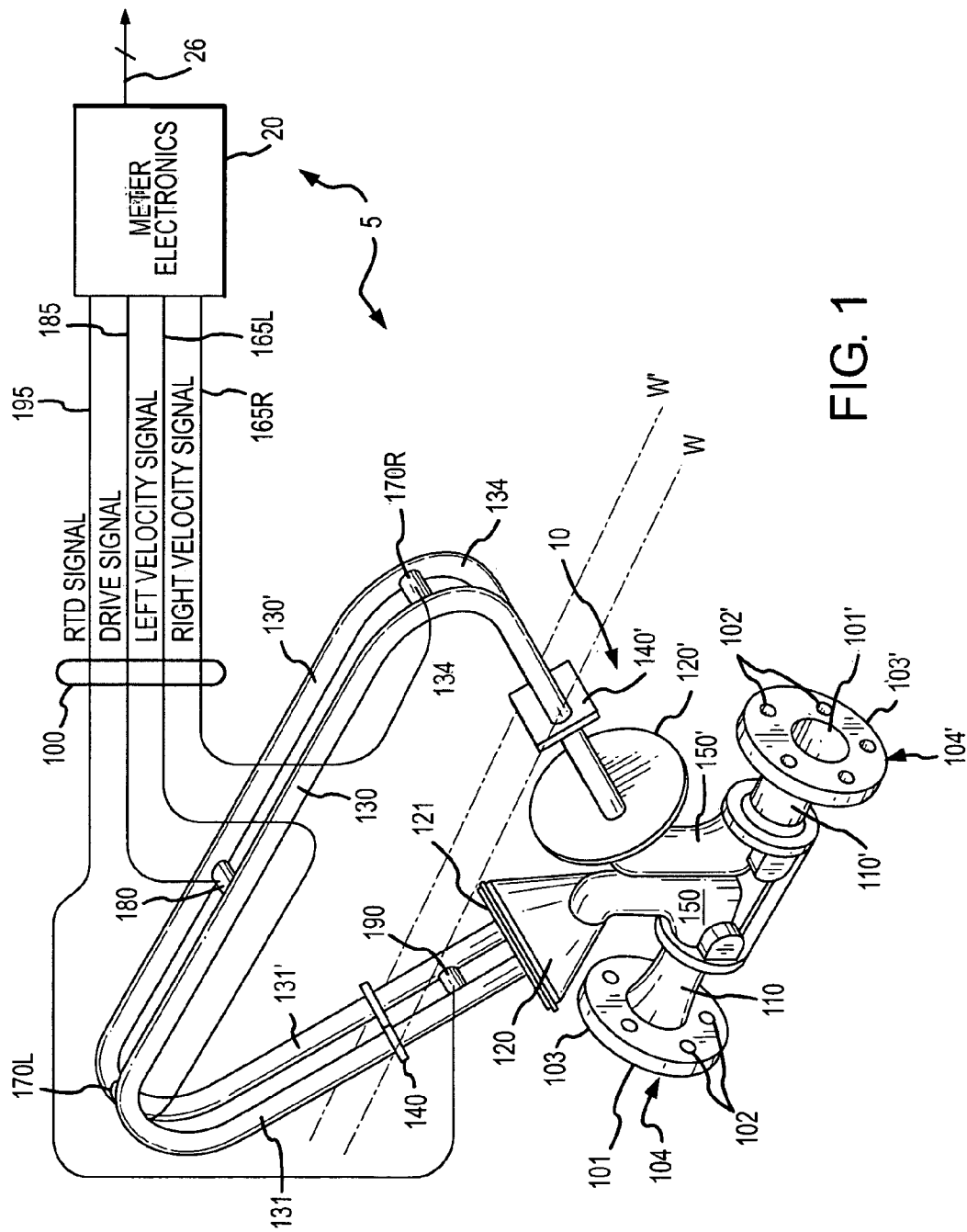
FIG. 1 illustrates a Coriolis flow meter in an example of the invention.

FIG. 1 shows a Coriolis flow meter 5 comprising a meter assembly 10 and meter electronics 20. Meter assembly 10 responds to mass flow rate and density of a process material. Meter electronics 20 is connected to meter assembly 10 via leads 100 to provide density, mass flow rate, and temperature information over path 26, as well as other information not relevant to the present invention. A Coriolis flow meter structure is described although it is apparent to those skilled in the art that the present invention could be practiced as a vibrating tube densitometer without the additional measurement capability provided by a Coriolis mass flow meter.

Meter assembly 10 includes a pair of manifolds 150 and 150', flanges 103 and 103' having flange necks 110 and 110', a pair of parallel flow tubes 130 and 130', drive mechanism 180, temperature sensor 190, and a pair of velocity sensors 170L and 170R. Flow tubes 130 and 130' have two essentially straight inlet legs 131 and 131' and outlet legs 134 and 134' which converge towards each other at flow tube mounting blocks 120 and 120'. Flow tubes 130 and 130' bend at two symmetrical locations along their length and are essentially parallel throughout their length. Brace bars 140 and 140' serve to define the axis W and W' about which each flow tube oscillates.

The side legs 131, 131' and 134, 134' of flow tubes 130 and 130' are fixedly attached to flow tube mounting blocks 120 and 120' and these blocks, in turn, are fixedly attached to manifolds 150 and 150'. This provides a continuous closed material path through Coriolis meter assembly 10.

When flanges 103 and 103', having holes 102 and 102' are connected, via inlet end 104 and outlet end 104' into a process line (not shown) which carries the process material that is being measured, material enters end 104 of the meter through an orifice 101 in flange 103 is conducted through manifold 150 to flow tube mounting block 120 having a surface 121. Within manifold 150 the material is divided and routed through flow tubes 130 and 130'. Upon exiting flow tubes 130 and 130', the process material is recombined in a single stream within manifold 150' and is thereafter routed to exit end 104' connected by flange 103' having bolt holes 102' to the process line (not shown).

Flow tubes 130 and 130' are selected and appropriately mounted to the flow tube mounting blocks 120 and 120' so as to have substantially the same mass distribution, moments of inertia and Young's modulus about bending axes W-W and W'-W', respectively. These bending axes go through brace bars 140 and 140'. Inasmuch as the Young's modulus of the flow tubes change with temperature, and this change affects the calculation of flow and density, resistive temperature detector (RTD) 190 is mounted to flow tube 130', to continuously measure the temperature of the flow tube. The temperature of the flow tube and hence the voltage appearing across the RTD for a given current passing therethrough is governed by the temperature of the material passing through the flow tube. The temperature dependent voltage appearing across the RTD is used in a well known method by meter electronics 20 to compensate for the change in elastic modulus of flow tubes 130 and 130' due to any changes in flow tube temperature. The RTD is connected to meter electronics 20 by lead 195.

Both flow tubes 130 and 130' are driven by driver 180 in opposite directions about their respective bending axes W and W' and at what is termed the first out-of-phase bending mode of the flow meter. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

Meter electronics 20 receives the RTD temperature signal on lead 195, and the left and right velocity signals appearing on leads 165L and 165R, respectively. Meter electronics 20 produces the drive signal appearing on lead 185 to drive element 180 and vibrate tubes 130 and 130'. Meter electronics 20 processes the left and right velocity signals and the RTD signal to compute the mass flow rate and the density of the material passing through meter assembly 10. This information, along with other information, is applied by meter electronics 20 over path 26 to utilization means [29].

Figure 2:
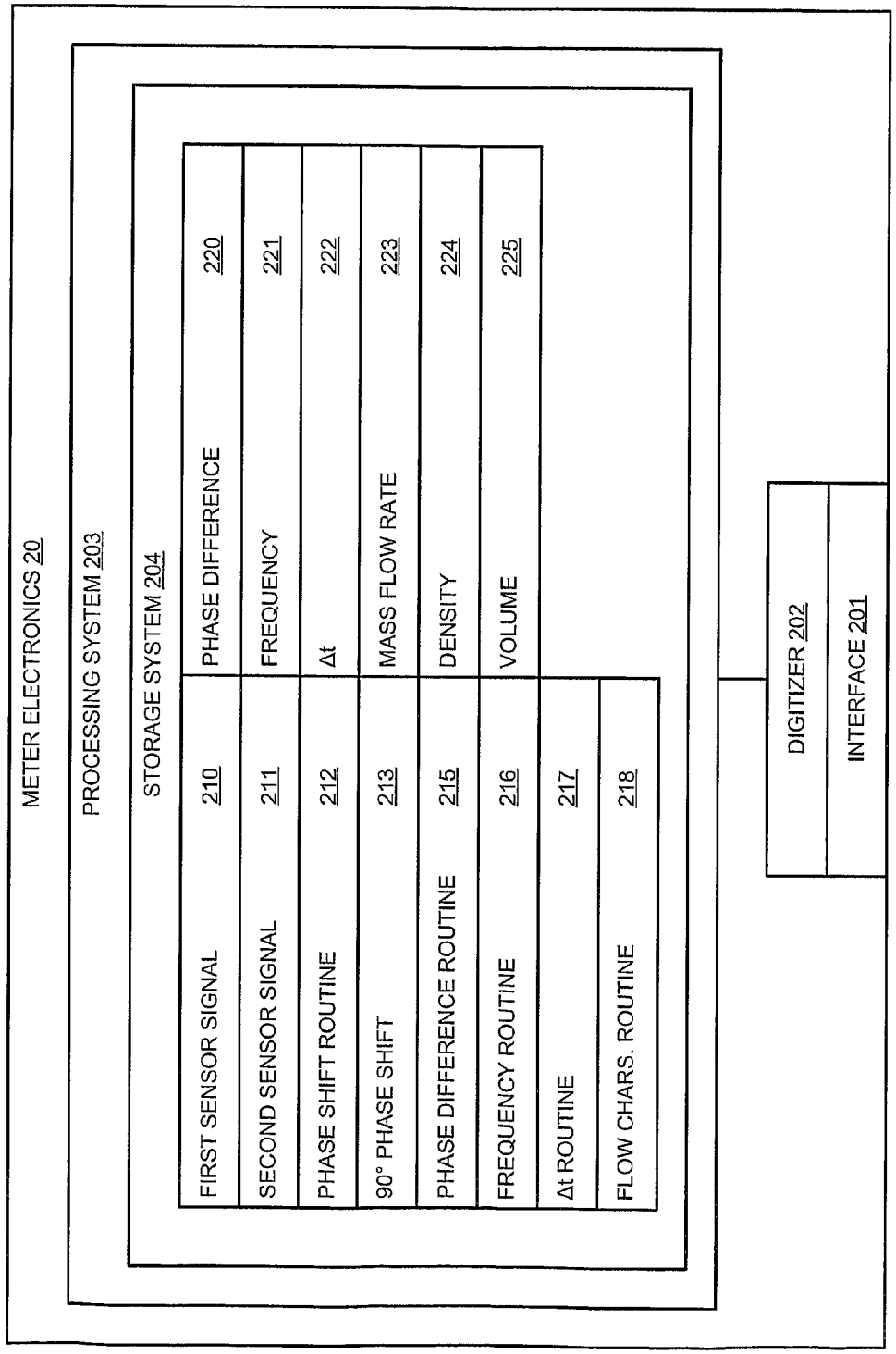
FIG. 2 shows meter electronics according to an embodiment of the invention.

FIG. 2 shows meter electronics 20 according to an embodiment of the invention. The meter electronics 20 can include an interface 201 and a processing system 203. The meter electronics 20 receives first and second sensor signals from the meter assembly 10, such as pickoff/velocity sensor signals. The meter electronics 20 processes the first and second sensor signals in order to obtain flow characteristics of the flow material flowing through the meter assembly 10. For example, the meter electronics 20 can determine one or more of a phase difference, a frequency, a time difference ($\Delta t$), a density, a mass flow rate, and a volume flow rate from the sensor signals, for example. In addition, other flow characteristics can be determined according to the invention. The determinations are discussed below.

The phase difference determination and the frequency determination are much faster and more accurate and reliable than such determinations in the prior art. In one embodiment, the phase difference determination and the frequency determination are directly derived from a phase shift of only one sensor signal, without the need for any frequency reference signal. This advantageously reduces the processing time required in order to compute the flow characteristics. In another embodiment, the phase difference is derived from phase shifts of both sensor signals, while the frequency is derived from only one phase shift signal. This increases the accuracy of both flow characteristics, and both can be determined much faster than in the prior art.

The prior art frequency determination methods typically take 1-2 seconds to perform. In contrast, the frequency determination according to the invention can be performed in as little as 50 milliseconds (ms). Even faster frequency determination is contemplated, depending on the type and configuration of the processing system, the sampling rate of the vibrational response, the filter sizes, the decimation rates, etc. At the 50 ms frequency determination rate, the meter electronics 20 according to the invention can be about 40 times faster than the prior art.

The interface 201 receives the sensor signal from one of the velocity sensors 170L and 170R via the leads 100 of FIG. 1. The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 20 and external devices. The interface 201 can be capable of any manner of electronic, optical, or wireless communication.

The interface 201 in one embodiment is coupled with a digitizer 202, wherein the sensor signal comprises an analog sensor signal. The digitizer 202 samples and digitizes the analog sensor signal and produces a digital sensor signal. The digitizer 202 can also perform any needed decimation, wherein the digital sensor signal is decimated in order to reduce the amount of signal processing needed and to reduce the processing time. The decimation will be discussed in more detail below.

The processing system 203 conducts operations of the meter electronics 20 and processes flow measurements from the flow meter assembly 10. The processing system 203 executes one or more processing routines and thereby processes the flow measurements in order to produce one or more flow characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

The processing system 203 processes the sensor signal 210 in order to determine one or more flow characteristics from the sensor signal 210. The one or more flow characteristics can include a phase difference, a frequency, a time difference ($\Delta t$), a mass flow rate, and/or a density for the flow material, for example.

In the embodiment shown, the processing system 203 determines the flow characteristics from the two sensor signals 210 and 211 and the single sensor signal phase shift 213. The processing system 203 can determine at least the phase difference and the frequency from the two sensor signals 210 and 211 and the single phase shift 213. As a result, either a first or second phase shifted sensor signal (such as one of the upstream or downstream pickoff signals) can be processed by the processing system 203 according to the invention in order to determine a phase difference, a frequency, a time difference ($\Delta t$), and/or a mass flow rate for the flow material.

The storage system 204 can store flow meter parameters and data, software routines, constant values, and variable values. In one embodiment, the storage system 204 includes routines that are executed by the processing system 203. In one embodiment, the storage system 204 stores a phase shift routine 212, a phase difference routine 215, a frequency routine 216, a time difference ($\Delta t$) routine 217, and a flow characteristics routine 218.

In one embodiment, the storage system 204 stores variables used to operate the Coriolis flow meter 5. The storage system 204 in one embodiment stores variables such as the first sensor signal 210 and the second sensor signal 211, which are received from the velocity/pickoff sensors 170L and 170R. In addition, the storage system 204 can store a 90 degree phase shift 213 that is generated in order to determine the flow characteristics.

In one embodiment, the storage system 204 stores one or more flow characteristics obtained from the flow measurements. The storage system 204 in one embodiment stores flow characteristics such as a phase difference 220, a frequency 221, a time difference ($\Delta t$) 222, a mass flow rate 223, a density 224, and a volume flow rate 225, all determined from the sensor signal 210.

The phase shift routine 212 performs a 90 degree phase shift on an input signal, i.e., on the sensor signal 210. The phase shift routine 212 in one embodiment implements a Hilbert transform (discussed below).

The phase difference routine 215 determines a phase difference using the single 90 degree phase shift 213. Additional information can also be used in order to compute the phase difference. The phase difference in one embodiment is computed from the first sensor signal 210, the second sensor signal 211, and the 90 degree phase shift 213. The determined phase difference can be stored in the phase difference 220 of the storage system 204. The phase difference, when determined from the 90 phase shift 213, can be calculated and obtained much faster than in the prior art. This can provide a critical difference in flow meter applications having high flow rates or where multi-phase flows occur. In addition, the phase difference can be determined independent of the frequency of either sensor signal 210 or 211. Moreover, because the phase difference is determined independently of the frequency, an error component in the phase difference does not include an error component of the frequency determination, i.e., there is no compounding error in the phase difference measurement. Consequently, the phase difference error is reduced over a phase difference of the prior art.

The frequency routine 216 determines a frequency (such as that exhibited by either the first sensor signal 210 or the second sensor signal 211) from the 90 degree phase shift 213. The determined frequency can be stored in the frequency 221 of the storage system 204. The frequency, when determined from the single 90 phase shift 213, can be calculated and obtained much faster than in the prior art. This can provide a critical difference in flow meter applications having high flow rates or where multi-phase flows occur.

The time difference ($\Delta t$) routine 217 determines a time difference ($\Delta t$) between the first sensor signal 210 and the second sensor signal 211. The time difference ($\Delta t$) can be stored in the time difference ($\Delta t$) 222 of the storage system 204. The time difference ($\Delta t$) comprises substantially the determined phase divided by the determined frequency, and is therefore used to determine the mass flow rate.

The flow characteristics routine 218 can determine one or more flow characteristics. The flow characteristics routine 218 can use the determined phase difference 220 and the determined frequency 221, for example, in order to accomplish these additional flow characteristics. It should be understood that additional information may be required for these determinations, such as the mass flow rate or density, for example. The flow characteristics routine 218 can determine a mass flow rate from the time difference ($\Delta t$) 222, and therefore from the phase difference 220 and the frequency 221. The formula for determining mass flow rate is given in U.S. Pat. No. 5,027,662 to Titlow et al., and is incorporated herein by reference. The mass flow rate is related to the mass flow of flow material in the meter assembly 10. Likewise, the flow characteristics routine 218 can also determine the density 224 and/or the volume flow rate 225. The determined mass flow rate, density, and volume flow rate can be stored in the mass flow rate 223, the density 224, and the volume 225 of the storage system 204, respectively. In addition, the flow characteristics can be transmitted to external devices by the meter electronics 20.

Figure 3:
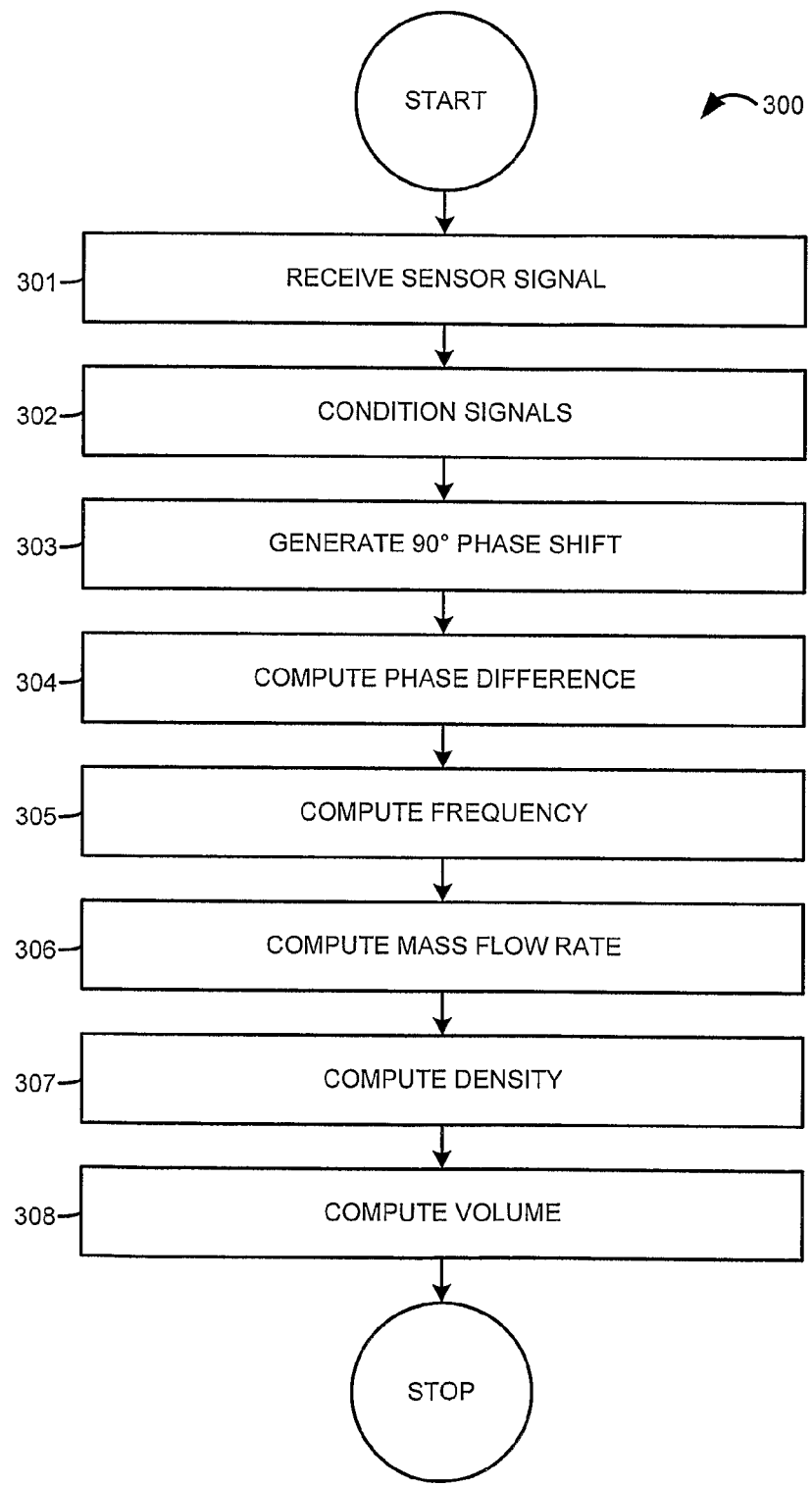
FIG. 3 is a flowchart of a method of processing a sensor signal in a Coriolis flowmeter according to an embodiment of the invention.

FIG. 3 is a flowchart 300 of a method of processing sensor signals in a Coriolis flowmeter according to an embodiment of the invention. In step 301, the first and second sensor signals are received. The first sensor signal can comprise either an upstream or downstream pickoff sensor signal.

In step 302, the sensor signals can be conditioned. In one embodiment, the conditioning can include filtering to remove noise and unwanted signals. In one embodiment, the filtering can comprise band-pass filtering centered around the expected fundamental frequency of the Coriolis flow meter 5. In addition, other conditioning operations can be performed, such as amplification, buffering, etc. If the sensor signals comprise analog signals, the step can further comprise any manner of sampling, digitization, and decimation that are performed in order to produce digital sensor signals.

In step 303, a single 90 degree phase shift is generated. The 90 degree phase shift comprises a 90 degree phase shift of the sensor signal. The 90 degree phase shift can be performed by any manner of phase shift mechanism or operation. In one embodiment, the 90 degree phase shift is performed using a Hilbert transform, operating on digital sensor signals.

In step 304, a phase difference is computed, using the single 90 degree phase shift. Additional information can also be used in order to compute the phase difference. In one embodiment, the phase difference is determined from the first sensor signal, the second sensor signal, and the single 90 degree phase shift. The phase difference comprises a phase difference in the response signal, i.e., in a pickoff sensor, that is seen due to the Coriolis effect in the vibrating meter assembly 10.

The resulting phase difference is determined without the need for any frequency value in the calculation. The resulting phase difference can be obtained much faster than a phase difference calculated using a frequency. The resulting phase difference has a greater accuracy than a phase difference calculated using a frequency.

In step 305, a frequency is computed. The frequency according to the invention is advantageously computed from the 90 degree phase shift. The frequency in one embodiment uses the 90 degree phase shift and the corresponding sensor signal from which the 90 degree phase shift is derived. The frequency is a vibrational response frequency of one of the first sensor signal and the second sensor signal (the frequencies of the two sensor signals are substantially identical in operation). The frequency comprises a vibrational frequency response of the flowtube or flowtubes to a vibration generated by the driver 180.

The frequency thus derived is obtained without the need for any independent frequency reference signal. The frequency is obtained from the single 90 degree phase shift in an operation that is much faster than in the prior art. The resulting frequency has a greater accuracy than a frequency calculated in the prior art.

In step 306, a mass flow rate of flow material is computed. The mass flow rate is computed from the resulting phase difference and the resulting frequency computed in steps 304 and 305. In addition, the mass flow rate computation can compute a time difference ($\Delta t$) from the phase difference and the frequency, with the time difference ($\Delta t$) being ultimately used to compute the mass flow rate.

In step 307, the density can optionally be determined. The density can be determined as one of the flow characteristics, and can be determined from the frequency, for example.

In step 308, the volume flow rate can optionally be determined. The volume flow rate can be determined as one of the flow characteristics, and can be determined from the mass flow rate and the density, for example.

Figure 4:
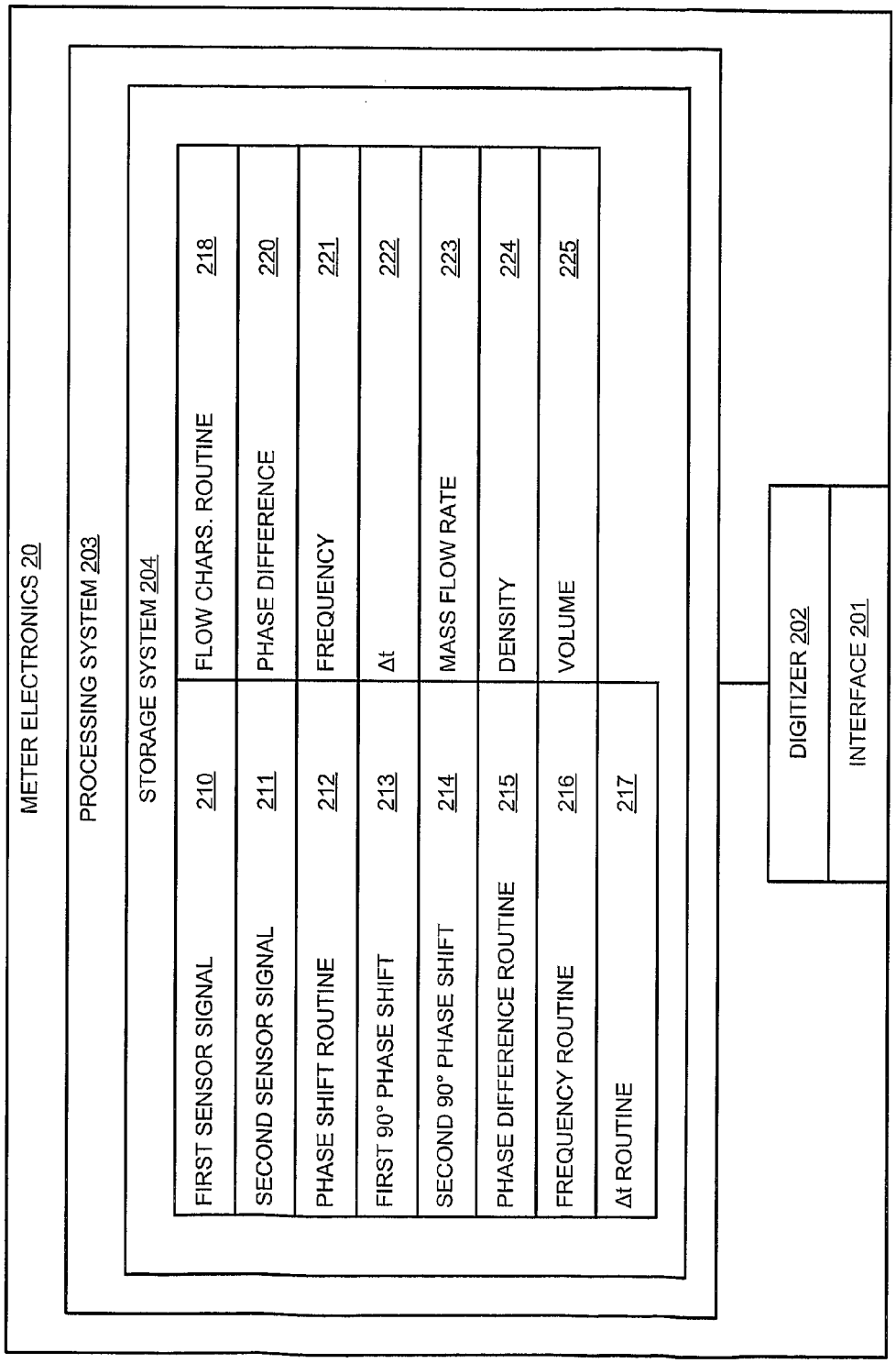
FIG. 4 shows the meter electronics according to an embodiment of the invention.

FIG. 4 shows the meter electronics 20 according to an embodiment of the invention. The elements in common with FIG. 2 share the same reference numbers.

The meter electronics 20 in this embodiment includes the first sensor signal 210 and the second sensor signal 211. The processing system 203 processes the first and second (digital) sensor signals 210 and 211 in order to determine one or more flow characteristics from the signals. As previously discussed, the one or more flow characteristics can include a phase difference, a frequency, a time difference ($\Delta t$), a mass flow rate, a density, and/or a volume flow rate for the flow material.

In the embodiment shown, the processing system 203 determines the flow characteristics from only the two sensor signals 210 and 211, without the need for any external frequency measurement and without the need for an external frequency reference signal. The processing system 203 can determine at least the phase difference and the frequency from the two sensor signals 210 and 211.

As was previously discussed, the storage system 204 stores a phase shift routine 212, a phase difference routine 215, a frequency routine 216, a time difference ($\Delta t$) routine 217, and a flow characteristics routine 218. The storage system 204 stores the first sensor signal 210 and the second sensor signal 211. The storage system 204 also stores a first 90 degree phase shift 213 and a second 90 degree phase shift that are generated from the sensor signals in order to determine the flow characteristics. As was previously discussed, the storage system 204 stores the phase difference 220, the frequency 221, the time difference ($\Delta t$) 222, the mass flow rate 223, the density 224, and the volume flow rate 225.

The phase shift routine 212 performs a 90 degree phase shift on an input signal, including on the first sensor signal 210 and on the second sensor signal 211. The phase shift routine 212 in one embodiment implements a Hilbert transform (discussed below).

The phase difference routine 215 determines a phase difference using the first 90 degree phase shift 213 and the second 90 degree phase shift 214. Additional information can also be used in order to compute the phase difference. The phase difference in one embodiment is computed from the first sensor signal 210, the second sensor signal 211, the first 90 degree phase shift 213, and the second 90 degree phase shift 214. The determined phase difference can be stored in the phase difference 220 of the storage system 204, as previously discussed. The phase difference, when determined using the first and second 90 degree phase shifts, can be calculated and obtained much faster than in the prior art. This can provide a critical difference in flow meter applications having high flow rates or where multi-phase flows occur. In addition, the phase difference can be determined independent of the frequency of the sensor signals 210 and 211. Moreover, because the phase difference is determined independently of the frequency, an error component in the phase difference does not suffer from an error component of the frequency determination, i.e., there is no compounding error in the phase difference measurement. Consequently, the phase difference error is reduced over a phase difference of the prior art.

The frequency routine 216 determines a frequency (such as that exhibited by either the first sensor signal 210 or the second sensor signal 211) from the first 90 degree phase shift 213 and the second 90 degree phase shift 214. The determined frequency can be stored in the frequency 221 of the storage system 204, as previously discussed. The frequency, when determined from the first and second 90 phase shifts, can be calculated and obtained much faster than in the prior art. This can provide a critical difference in flow meter applications having high flow rates or where multi-phase flows occur.

The time difference ($\Delta t$) routine 217 determines a time difference ($\Delta t$) between the first sensor signal 210 and the second sensor signal 211. The time difference ($\Delta t$) can be stored in the time difference ($\Delta t$) 222 of the storage system 204, as previously discussed. The time difference ($\Delta t$) comprises substantially the determined phase divided by the determined frequency, and is therefore used to determine the mass flow rate.

The flow characteristics routine 218 can determine one or more of the mass flow rate, the density, and/or the volume flow rate, as previously discussed.

Figure 5:
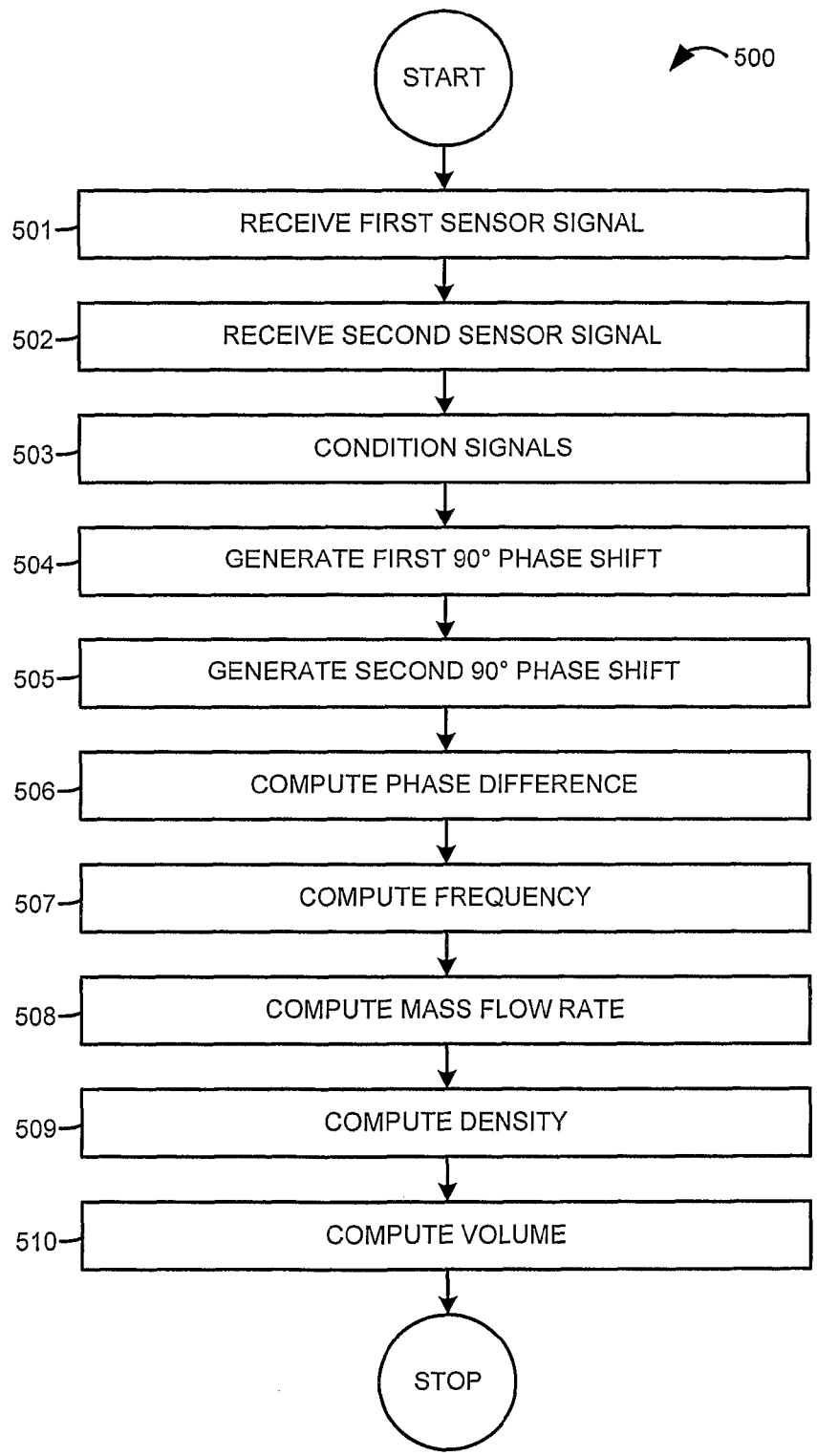
FIG. 5 is a flowchart of a method of processing first and second sensor signals in a Coriolis flowmeter according to an embodiment of the invention.

FIG. 5 is a flowchart 500 of a method of processing first and second sensor signals in a Coriolis flowmeter according to an embodiment of the invention. In step 501, the first sensor signal is received. In one embodiment, the first sensor signal comprises either an upstream or downstream pickoff sensor signal.

In step 502, the second sensor signal is received. In one embodiment, the second sensor signal comprises either a downstream or upstream pickoff sensor signal (i.e., the opposite of the first sensor signal).

In step 503, the sensor signals can be conditioned. In one embodiment, the conditioning can include filtering to remove noise and unwanted signals. In one embodiment, the filtering can comprise band-pass filtering, as previously discussed. In addition, other conditioning operations can be performed, such as amplification, buffering, etc. If the sensor signals comprise analog signals, the step can further comprise any manner of sampling, digitization, and decimation that are performed in order to produce digital sensor signals.

In step 504, a first 90 degree phase shift is generated. The first 90 degree phase shift comprises a 90 degree phase shift of the first sensor signal. The 90 degree phase shift can be performed by any manner of mechanism or operation. In one embodiment, the 90 degree phase shift is performed using a Hilbert transform, operating on digital sensor signals.

In step 505, a second 90 degree phase shift is generated. The second 90 degree phase shift comprises a 90 degree phase shift of the second sensor signal. As in the first 90 degree phase shift, the 90 degree phase shift can be performed by any manner of mechanism or operation.

In step 506, a phase difference is computed between the first sensor signal and the second sensor signal, using the first 90 degree phase shift and the second 90 degree phase shift. Additional information can also be used in order to compute the phase difference. In one embodiment, the phase difference is determined from the first sensor signal, the second sensor signal, the first 90 degree phase shift, and the second 90 degree phase shift. The phase difference comprises a phase difference in the response signal, i.e., in the two pickoff sensors, that is seen due to the Coriolis effect in the vibrating meter assembly 10.

The resulting phase difference is determined without the need for any frequency value in the calculation. The resulting phase difference can be obtained much faster than a phase difference calculated using a frequency. The resulting phase difference has a greater accuracy than a phase difference calculated using a frequency.

In step 507, a frequency is computed. The frequency according to the invention is advantageously computed from the first 90 degree phase shift and the second 90 degree phase shift. The frequency in one embodiment uses the 90 degree phase shift and the corresponding sensor signal from which the 90 degree phase shift is derived. The frequency is a vibrational response frequency of one of the first sensor signal and the second sensor signal (the frequencies of the two sensor signals are substantially identical in operation). The frequency comprises a vibrational frequency response of the flowtube or flowtubes to a vibration generated by the driver 180.

The frequency thus derived is obtained without the need for any independent frequency reference signal. The frequency is obtained from the 90 degree phase shifts in an operation that is much faster than in the prior art. The resulting frequency has a greater accuracy than a frequency calculated in the prior art.

In step 508, a mass flow rate of flow material is computed. The mass flow rate is computed from the resulting phase difference and the resulting frequency computed in steps 506 and 507. In addition, the mass flow rate computation can compute a time difference (Δt) from the phase difference and the frequency, with the time difference (Δt) being ultimately used to compute the mass flow rate.

In step 509, the density can optionally be determined, as previously discussed.

In step 510, the volume flow rate can optionally be determined, as previously discussed.

Figure 6:
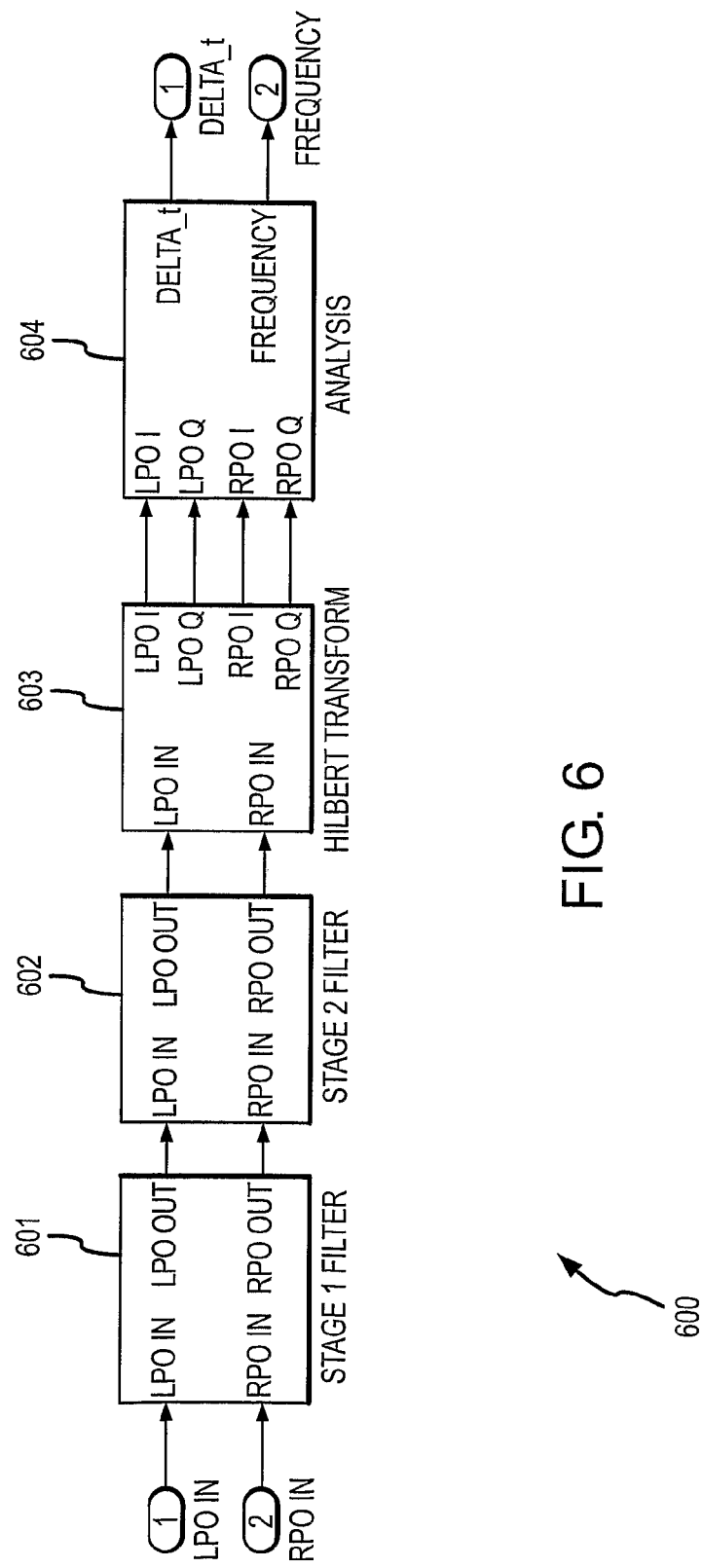
FIG. 6 is a block diagram of a portion of the processing system according to an embodiment of the invention.

FIG. 6 is a block diagram 600 of a portion of the processing system 203 according to an embodiment of the invention. In the figure, the blocks represent either processing circuitry or processing actions/routines. The block diagram 600 includes a stage 1 filter block 601, a stage 2 filter block 602, a Hilbert transform block 603, and an analysis block 604. The LPO and RPO inputs comprise the left pickoff signal input and the right pickoff signal input. Either the LPO or the RPO can comprise a first sensor signal.

In one embodiment, the stage 1 filter block 601 and the stage 2 filter block 602 comprise digital Finite Impulse Response (FIR) polyphase decimation filters, implemented in the processing system 203. These filters provide an optimal method for filtering and decimating one or both sensor signals, with the filtering and decimating being performed at the same chronological time and at the same decimation rate. Alternatively, the stage 1 filter block 601 and the stage 2 filter block 602 can comprise Infinite Impulse Response (IIR) filters or other suitable digital filters or filter processes. However, it should be understood that other filtering processes and/or filtering embodiments are contemplated and are within the scope of the description and claims.

Figure 7:
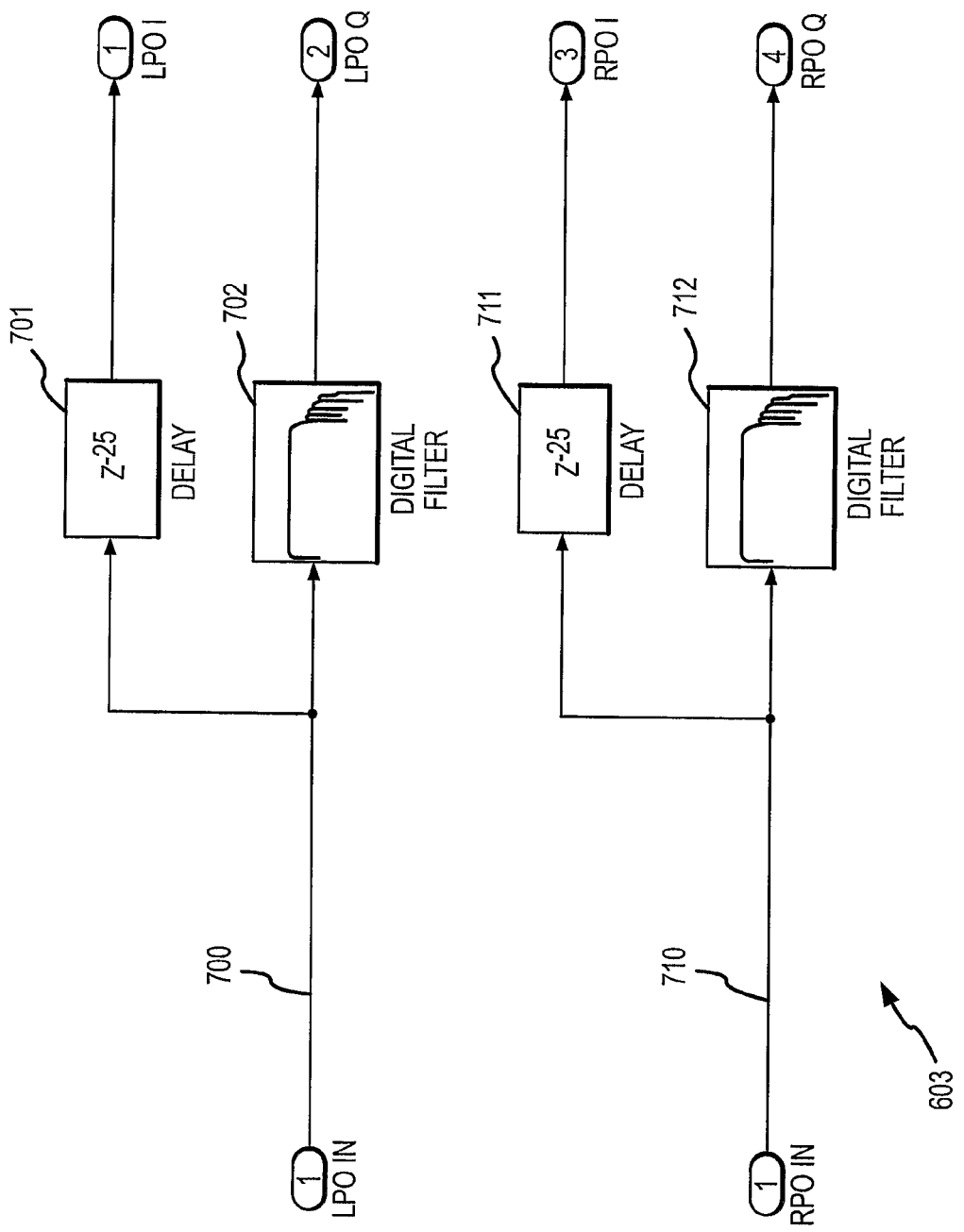
FIG. 7 shows detail of the Hilbert transform block according to an embodiment of the invention.

FIG. 7 shows detail of the Hilbert transform block 603 according to an embodiment of the invention. In the embodiment shown, the Hilbert transform block 603 includes a LPO branch 700 and a RPO branch 710. The LPO branch 700 includes a LPO delay block 701 in parallel with a LPO filter block 702. Likewise, the RPO branch includes an RPO delay block 711 in parallel with an RPO filter block 712. The LPO delay block 701 and the RPO delay block 711 introduce sampling delays. The LPO delay block 701 and the RPO delay block 711 therefore select LPO and RPO digital signal samples that are chronologically later in time that the LPO and RPO digital signal samples that are filtered by the LPO filter block 702 and the RPO filter block 712. The LPO filter block 702 and the RPO filter block 712 perform a 90 degree phase shift on the inputted digital signal samples.

The Hilbert transform block 603 is a first step to providing the phase measurement. The Hilbert transform block 603 receives the filtered, decimated LPO and RPO signals and performs a Hilbert transform. The Hilbert transform produces 90 degree phase-shifted versions of the LPO and RPO signals, i.e., it produces quadrature (Q) components of the original, in-phase (I) signal components. The output of the Hilbert transform block 603 therefore provides the new quadrature (Q) components LPO Q and RPO Q, along with the original, in-phase (I) signal components LPO I and RPO I.

The inputs to the Hilbert transform block 603 can be represented as:

$$LPO = A_{lpo} \cos(\omega t) \tag{2}$$

$$RPO = A_{rpo} \cos(\omega t + \phi) \tag{3}$$

Using the Hilbert transform the output becomes:

$$LPO_{hilbert} = A_{lpo} \sin(\omega t) \tag{4}$$

$$RPO_{hilbert} = A_{rpo} \sin(\omega t + \phi)] \tag{5}$$

Combining the original terms with the output of the Hilbert transform yields:

$$LPO = A_{lpo}[\cos(\omega t) + i \sin(\omega t)] = A_{lpo} e^{j(\omega t)} \tag{6}$$

$$RPO = A_{rpo}[\cos(\omega t + \phi) + i \sin(\omega t + \phi)] = A_{rpo} e^{j(\omega t + \phi)} \tag{7}$$

FIGS. 8 and 9 are block diagrams of two independent branches of the analysis block 604 according to an embodiment of the invention. The analysis block 604 is the final stage of the frequency, differential phase, and delta T (Δt) measurement. FIG. 8 is phase portion 604a comprising a first branch that determines a phase difference from the in-phase (I) and quadrature (Q) components. FIG. 9 is a frequency portion 604b that determines a frequency from the in-phase (I) and quadrature (Q) components of a single sensor signal. The single sensor signal can comprise the LPO signal, as shown, or can alternatively comprise the RPO signal.

In the embodiment of FIG. 8, the phase portion 604a of the analysis block 604 includes join blocks 801a and 801b, a conjugate block 802, a complex multiplication block 803, a filter block 804, and a phase angle block 805.

The join blocks 801a and 801b receive both in-phase (I) and quadrature (Q) components of a sensor signal and pass them on. The conjugate block 802 performs a complex conjugate on a sensor signal (here the LPO signal), and forms a negative of the imaginary signal. The complex multiplication block 803 multiplies the RPO signal and the LPO signal, implementing equation (8) below. The filter block 804 implements a digital filter, such as the FIR filter discussed above. The filter block 804 can comprise a polyphase decimation filter that is used to remove harmonic content from the in-phase (I) and quadrature (Q) components of the sensor signal, as well as to decimate the signal. The filter coefficients can be chosen to provide decimation of the inputted signal, such as decimation by a factor of 10, for example. The phase angle block 805 determines the phase angle from the in-phase (I) and quadrature (Q) components of the LPO signal and the RPO signal. The phase angle block 805 implements equation (11) shown below.

The phase portion 604a shown in FIG. 8 implements the following equation:

$$\overline{LPO} \times RPO = A_{lpo} e^{-j(\omega t)} \times A_{Rpo} e^{j(\omega t + \phi)} = A_{lpo} \times A_{Rpo} e^{j(-\omega t + \omega t + \phi)} \tag{8}$$

where $\overline{LPO}$ is the complex conjugate of LPO. Assuming that:

$$A_{Rpo} = A_{Lpo} = A \tag{9}$$

then:

$$\overline{LPO} \times RPO = A^2 e^{j(\phi)} = A^2[\cos(\phi) + i \sin(\phi)] \tag{10}$$

The resulting differential phase angle is:

$$\phi = \tan^{-1}\left[\frac{\sin(\phi)}{\cos(\phi)}\right] \tag{11}$$

FIG. 9 is a block diagram of a frequency portion 604b of the analysis block 604 according to the invention. The frequency portion 604b can operate on either the left or right pickoff signal (LPO or RPO). The frequency portion 604*b* in the embodiment shown includes a join block 901, a complex conjugate block 902, a sampling block 903, a complex multiplication block 904, a filter block 905, a phase angle block 906, a constant block 907, and a division block 908.

As previously discussed, the join block 901 receives both in-phase (I) and quadrature (Q) components of a sensor signal and passes them on. The conjugate block 902 performs a complex conjugate on a sensor signal, here the LPO signal, and forms a negative of the imaginary signal. The delay block 903 introduces a sampling delay into the frequency portion 604*b*, and therefore selects a digital signal sample that is chronologically older in time. This older digital signal sample is multiplied with the current digital signal in the complex multiplication block 904. The complex multiplication block 904 multiplies the LPO signal and the LPO conjugate signal, implementing equation (12) below. The filter block 905 implements a digital filter, such as the FIR filter previously discussed The filter block 905 can comprise a polyphase decimation filter that is used to remove harmonic content from the in-phase (I) and quadrature (Q) components of the sensor signal, as well as to decimate the signal. The filter coefficients can be chosen to provide decimation of the inputted signal, such as decimation by a factor of 10, for example. The phase angle block 906 determines a phase angle from the in-phase (I) and quadrature (Q) components of the LPO signal. The phase angle block 906 implements a portion of equation (13) below. The constant block 907 supplies a factor comprising a sample rate $F_S$ divided by two pi, as shown in equation (14). The division block 908 performs the division operation of equation (14).

The frequency portion 604*b* implements the following equation:

$$\overline{LPO}_{(n-1)} \times LPO_{(n)} = A_{lpo} e^{-j(\omega t - 1)} \times A_{Lpo} e^{j(\omega t)} = A^2_{lpo} e^{j(\omega t - \omega t - 1)} \quad (12)$$

The angle between two consecutive samples is therefore:

$$\omega t - \omega t_{-1} = \tan^{-1}\left[\frac{\sin(\omega t - \omega t_{-1})}{\cos(\omega t - \omega t_{-1})}\right] \quad (13)$$

which is the radian frequency of the left pick-off. Converting to Hz:

$$f_{lpo} = \frac{(\omega t - \omega t_{-1}) \times Fs}{2\pi} \quad (14)$$

where "Fs" is the rate of the Hilbert transform block 603. In the example previously discussed, "Fs" is about 2 kHz.

Figure 10:
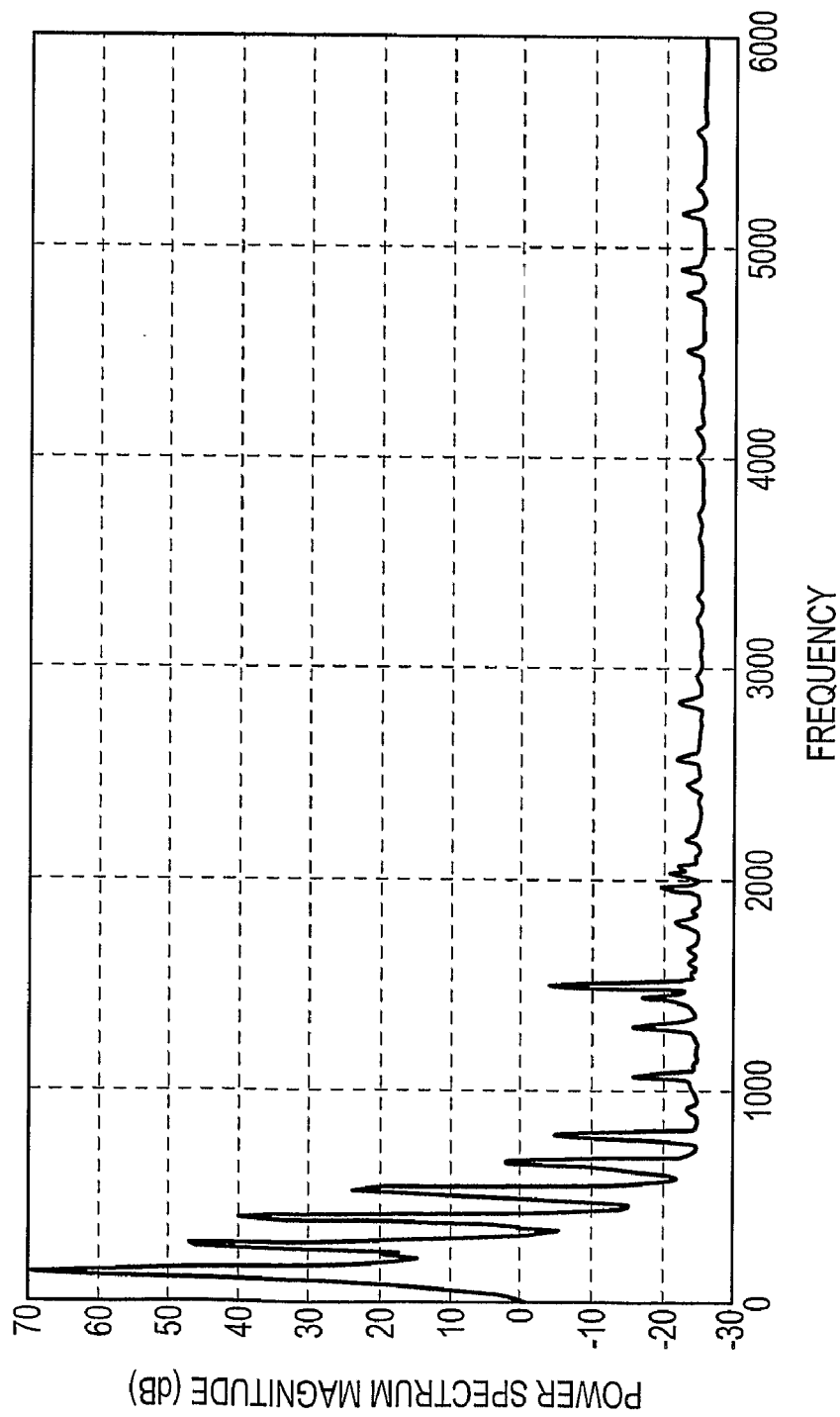
FIG. 10 is a power spectrum density plot of a pick-off sensor signal of a flow meter under normal conditions.

FIG. 10 is a power spectrum density plot of a pick-off sensor signal of a flow meter under normal conditions. The fundamental frequency of the flowmeter is the tallest spike of the graph and is located at about 135 Hz. The figure also shows several other large spikes in the frequency spectrum (the first non-fundamental mode is the twist mode at a frequency of about 1.5 times the frequency of the fundamental mode). These spikes comprise harmonic frequencies of the flowmeter and also comprise other, undesirable sensor modes (i.e., a twist mode, a second bend mode, etc.).

Figure 11:
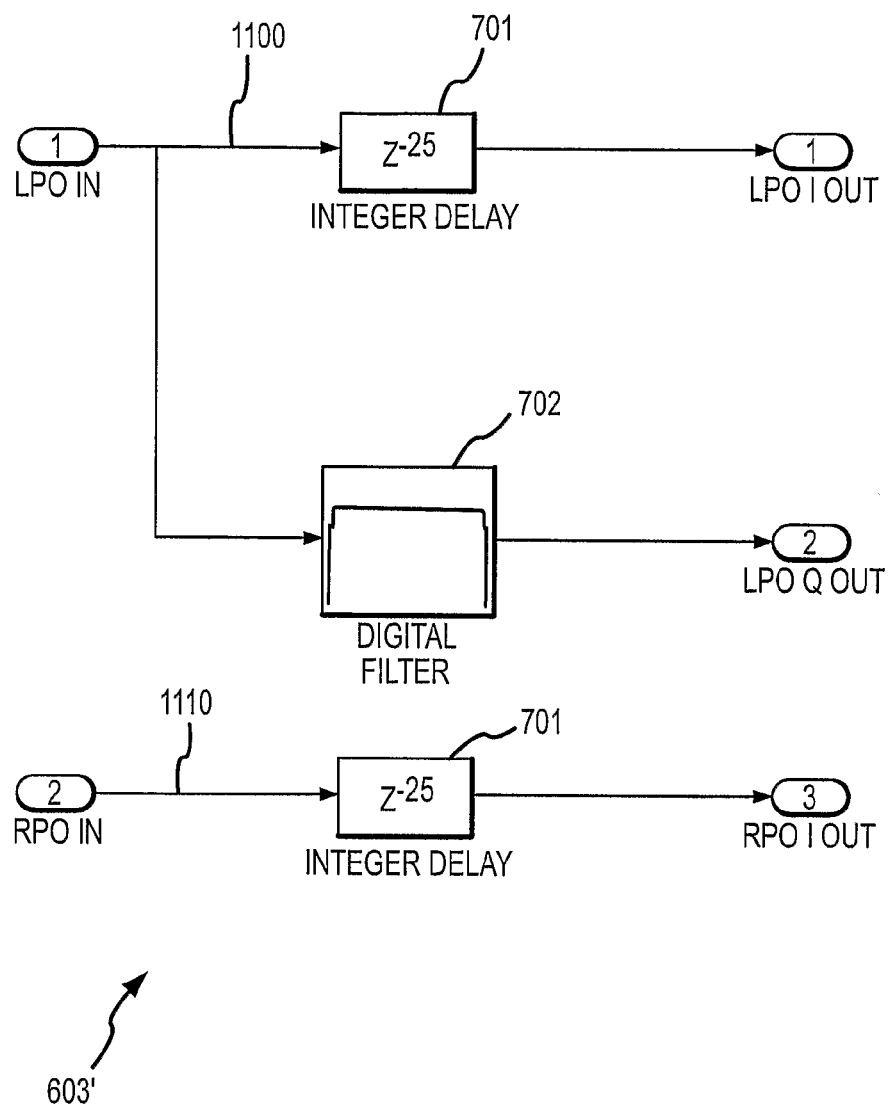
FIG. 11 shows a Hilbert transform block according to the single phase shift embodiment.

FIG. 11 shows an alternative Hilbert transform block 603' according to a single phase shift embodiment. The Hilbert transform block 603' in this embodiment includes a LPO branch 1100 and a RPO branch 1110. The LPO branch 1100 includes a delay block 701 in parallel with a filter block 702. The RPO branch 1110 in this embodiment includes only a delay block 701. As before, the delay blocks 701 introduce sampling delays. As before, the filter block 702 performs a 90 degree phase shift on the inputted digital signal sample. It should be understood that alternatively the Hilbert transform block 603' could phase shift just the RPO signal.

This processing embodiment uses the Hilbert transform/phase shift of only one sensor signal in order to derive both the frequency and the phase difference (see FIGS. 2-3). This significantly reduces the number of computations needed to perform a phase measurement and significantly reduces the number of computations needed to obtain the mass flow rate.

In this embodiment, the output of the Hilbert transform block 603' will provide the quadrature (Q) component of either the left or right sensor signal, but not both. In the example below, the LPO signal is phase shifted.

$$LPO = A_{lpo} \cos(\omega t) \quad (26)$$

$$RPO = A_{rpo} \cos(\omega t + \phi) \quad (27)$$

Using the Hilbert transform, the output becomes:

$$LPO_{hilbert} = A_{lpo} \sin(\omega t) \quad (28)$$

$$RPO = A_{rpo} \cos(\omega t + \phi) \quad (29)$$

Combining the LPO original term with the output of the Hilbert transform (i.e., with the 90 phase shift) yields:

$$LPO = A_{lpo}[\cos(\omega t) + i \sin(\omega t)] = A_{lpo} e^{j(\omega t)} \quad (30)$$

while the RPO stays the same:

$$RPO = A_{rpo} \cos(\omega t + \phi)$$
$$= A_{rpo}\left[\frac{e^{j(\omega t + \phi)} + e^{-j(\omega t + \phi)}}{2}\right] \quad (31)$$

Figure 12:
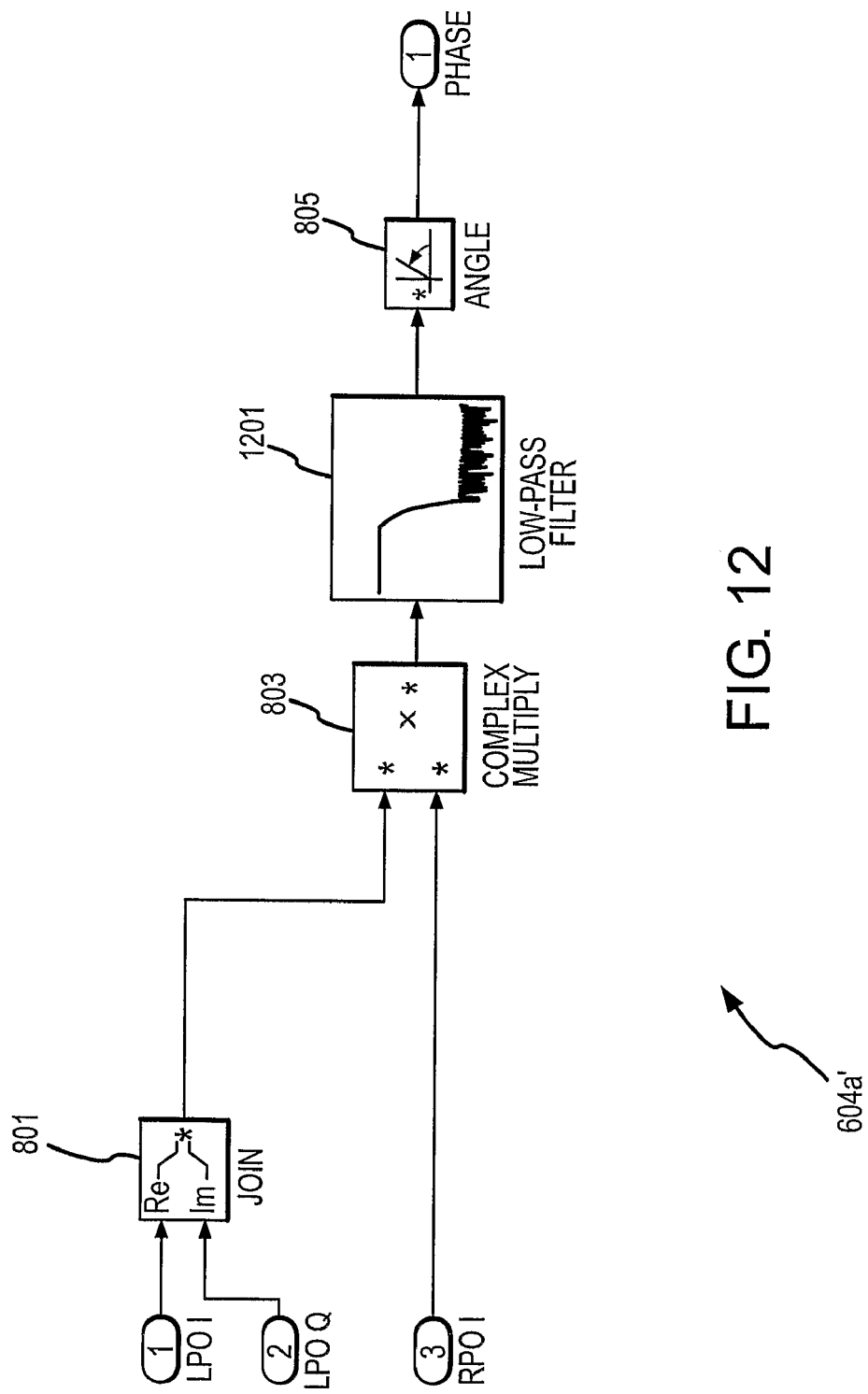
FIG. 12 shows the analysis block for the single phase shift embodiment.

FIG. 12 shows the analysis block 604*a'* for the single phase shift embodiment. The analysis block 604*a'* in this embodiment includes one join block 801, the complex multiplication block 803, a low-pass filter block 1201, and a phase angle block 805. The analysis block 604*a'* in this embodiment implements the following equation:

$$LPO \times RPO = A_{lpo} e^{-j(\omega t)} \times A_{rpo}\left[\frac{e^{j(\omega t + \phi)} + e^{-j(\omega t + \phi)}}{2}\right] \quad (32)$$
$$= \frac{A_{lpo} \times A_{Rpo}}{2}[e^{j(-\omega t + \omega t + \phi)} + e^{j(\omega t + \omega t + \phi)}]$$

The low-pass filter block 1201 comprises a low-pass filter that removes a high-frequency component produced by the complex multiplication block 803. The low-pass filter block 1201 can implement any manner of low-pass filtering operation. The result of the multiplication operation produces two terms. The (−ωt+ωt+Ø) term combines and simplifies to a phase-only Ø term (a DC result), since the (−ωt) and the (ωt) terms cancel each other out. The (ωt+ωt+Ø) simplifies to a (2ωt+Ø) term, at twice the frequency. Since the result is the sum of 2 terms, the high frequency (2ωt+Ø) term can be removed. The only signal of interest here is the DC term. The high frequency (2ωt+Ø) term can be filtered out of the result using a low-pass filter. The cut-off of the low-pass filter can be located anywhere between zero and 2ω).

After filtering, the result is:

$$LPO \times RPO = A^2 e^{j(\phi)} \quad (33)$$
$$= \frac{A^2}{2}[\cos(\phi) + i\sin(\phi)]$$

Therefore, the differential phase angle is:

$$\phi = \tan^{-1}\left[\frac{\sin(\phi)}{\cos(\phi)}\right]$$

By taking the Hilbert transform of one pick-off signal instead of two, the computational load needed to perform phase and frequency estimation in Coriolis mass flow meters is advantageously reduced. The phase and frequency can therefore be determined using two sensor signals, but using only one 90 degree phase shift.

Figure 13:
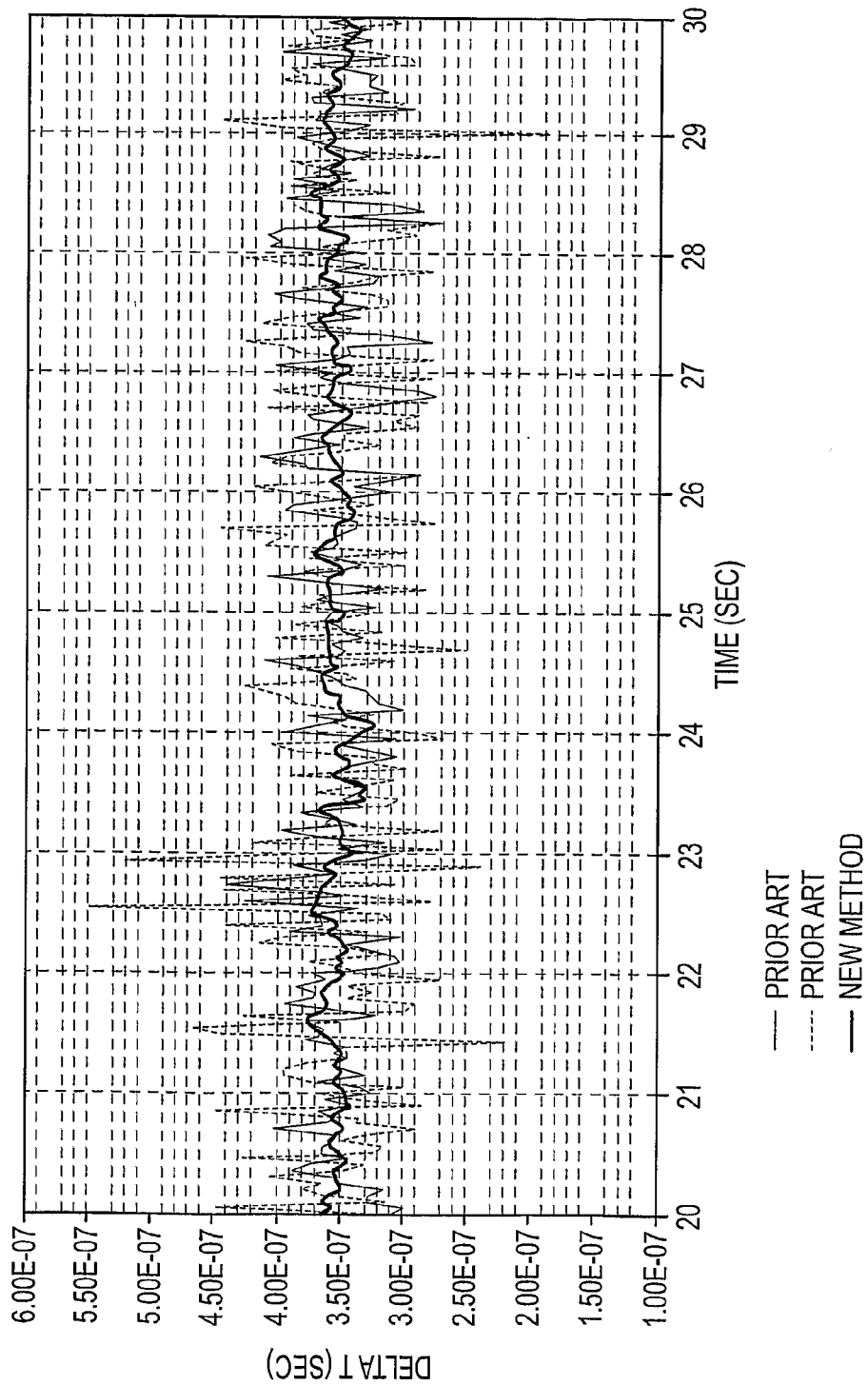
FIG. 13 shows the sensor processing of the invention as compared to the prior art, wherein a time difference (Δt) value of each is compared.

FIG. 13 shows the sensor processing of the invention as compared to the prior art, wherein a time difference (Δt) value of each is compared. The chart shows a flow material including a gas flow (i.e., gas bubbles, for example). Under this condition, the flow noise is substantially reduced in the new algorithm because of the rate of phase and frequency calculation. It can be seen from the graph that the result derived by the invention does not display the large peaks and valleys that are reflected in prior art (Δt) measurements.

Figure 14:
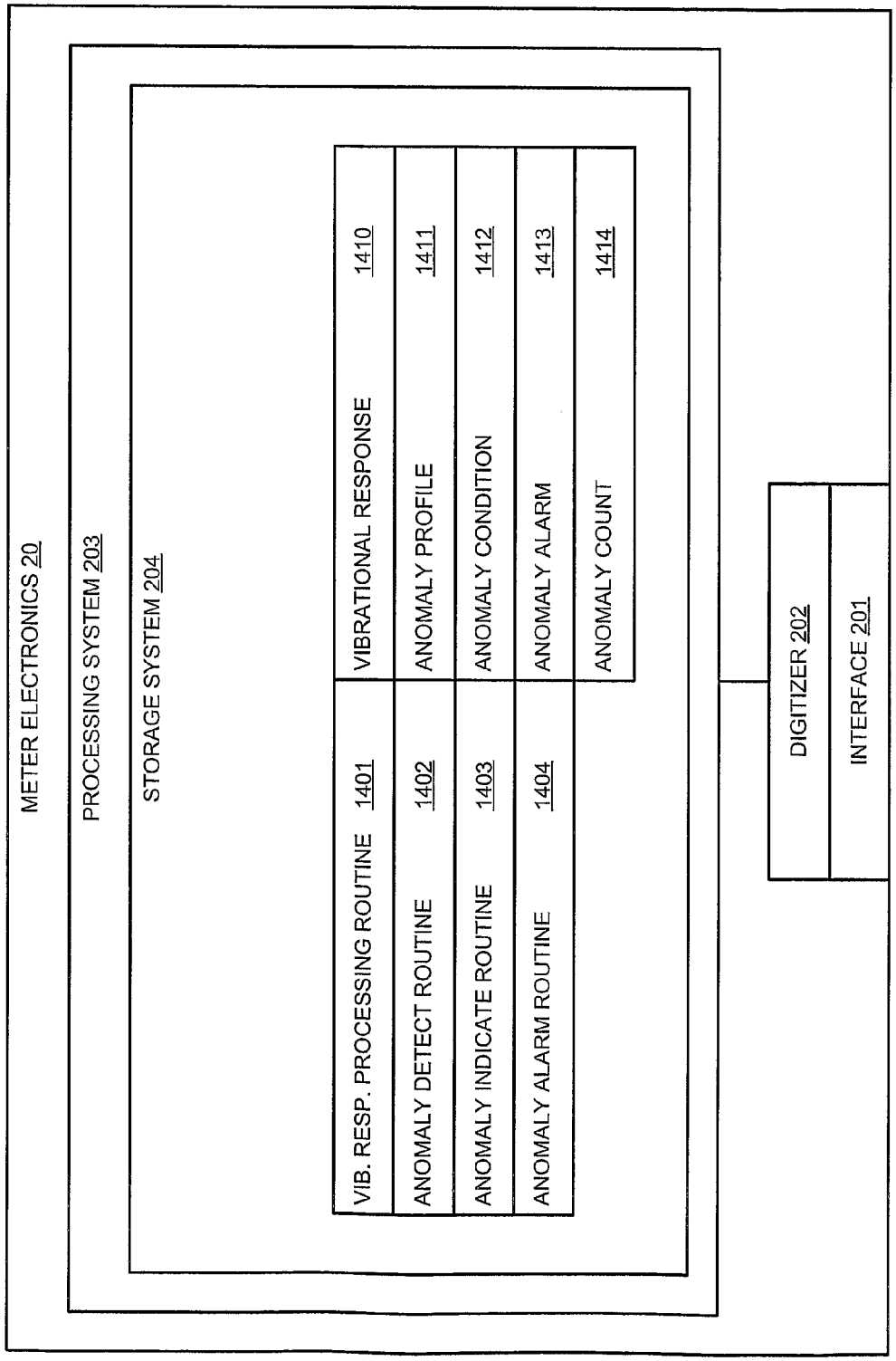
FIG. 14 shows the meter electronics according to another embodiment of the invention.

FIG. 14 shows the meter electronics 20 according to another embodiment of the invention. The meter electronics 20 of this embodiment can include the interface 201, the digitizer 202, the processing system 203, and the storage system 204, as previously discussed. The interface 201 receives a vibrational response of the flow material, with the vibrational response including at least a first sensor signal and a second sensor signal, as previously discussed. The processing system 203 in this embodiment is configured to receive the vibrational response from the interface 201, generate a ninety degree phase shift from the first sensor signal and generate at least one flow characteristic using at least the first sensor signal and the ninety degree phase shift. The first sensor signal can comprise any pick-off sensor signal from the meter assembly 10, as previously discussed. The processing system 203 is further configured to compare the at least one flow characteristic to at least one anomaly profile, detect a shift in the vibrational response if the at least one flow characteristic falls within the anomaly profile, and indicate an anomaly condition as a result of the detecting.

It should be understood that the meter electronics 20 of this figure can include various other components and/or routines discussed above. Components and/or routines in common with other embodiments share common reference numbers.

The meter electronics 20 can be in communication with the meter assembly 10, where the meter assembly 10 can comprise any manner of flow meter that generates at least a frequency response. In one embodiment, the meter assembly 10 comprises a Coriolis flow meter. In another embodiment, the meter assembly 10 comprises a vibrating densitometer.

The meter electronics 20 of this embodiment can store and execute processing routines. The processing routines in one embodiment include a vibrational response processing routine 1401, an anomaly detect routine 1402, an anomaly indicate routine 1403, and an anomaly alarm routine 1404. It should be understood that the processing system 203 can include other routines, such as the routines that were previously discussed.

The meter electronics 20 can include variables and working values. The meter electronics 20 of this embodiment includes a vibrational response 1410, one or more anomaly profiles 1411, an anomaly condition 1412, an anomaly alarm 1413, and an anomaly count 1414. It should be understood that the processing system 203 can include other variables, such as the variables that were previously discussed.

In operation, the meter electronics 20 processes a vibrational response that is received from the meter assembly 10 (see FIG. 1). The vibrational response can comprise a time-varying electronic signal(s) that is substantially continuously received and processed by the meter electronics 20. The vibrational response can include first and second sensor signals, such as signals from the pick-off sensors 170L and 170R. The meter electronics 20 can process the vibrational response in order to obtain one or more flow characteristics. The one or more flow characteristics can include, for example, a frequency response, a phase difference between sensor signals, a density, a mass flow rate, a volume flow rate, etc. Other flow characteristics are contemplated and are within the scope of the description and claims. The vibrational response, including any determined flow characteristics, and additionally a drive gain, can be used by the meter electronics 20 in order to detect an anomaly in the flow material flowing through the flow meter.

The flow characteristics, when determined using the single or dual phase shifts described above, can be quickly obtained, in contrast to the prior art. Moreover, the flow characteristics can be determined substantially instantaneously. Other flow characteristics can be determined using the frequency and the phase difference. The determinations of the flow characteristics can provide estimated flow characteristics. The nearly instantaneous flow characteristic determination(s) are advantageously available for use in other determinations, such as in the anomaly detection according to the invention. Because the flow characteristics can be substantially instantaneously determined, anomalies in the flow material can be quickly and accurately detected.

The anomaly can include entrained gas/air and/or bubbles in the flow material. The anomaly can include a foreign liquid in the flow material. The anomaly can include a solid in the flow material. The anomaly can include a two-phase or multi-phase flow material.

The flow characteristics will change when an anomaly passes through the meter assembly 10. When a significant anomaly moves through the flow meter, the meter will experience an instantaneous shift in frequency and a corresponding instantaneous shift in mass flow if the density/specific gravity of the anomaly differs from that of the flow material. The frequency of the meter assembly 10 can increase with lower density of the flow material (such as when entrained air is present, for example). Conversely, the frequency of the meter assembly 10 can decrease when high densities are present (such as when pieces of metal or other solids pass through, for example). Likewise, a density of the flow material can be used to detect anomalies such as air bubbles when the density characteristically decreases. For air bubbles, the frequency of the flow meter increases with the lower density fluid and the mass flow decreases due to the low mass of an air bubble. In addition, the phase difference and/or time delay can be used to detect such anomalies.

Figure 15:
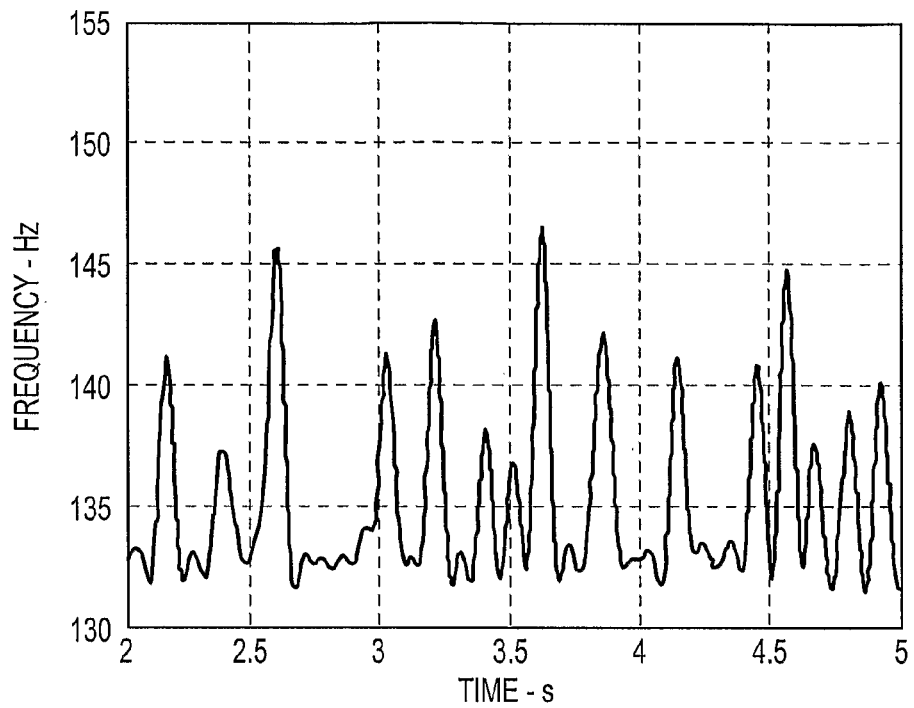
FIG. 15 is a graph of a frequency response versus time, wherein the upward spikes in the frequency flow characteristic represent anomalies in a flow material, such as air bubbles.

FIG. 15 is a graph of a frequency response versus time, wherein the upward spikes in the frequency flow characteristic represent anomalies in a flow material, such as air bubbles. The flow material in this example is water. The meter assembly 10, when filled with water as the flow material, exhibits a resonant frequency of about 132 Hz. The meter assembly 10 filled with air exhibits a resonant frequency of about 158 Hz. It can be seen from this graph that the meter assembly 10 is filled mostly with water. However, as indicated by the frequency spikes, fifteen air bubbles pass through the meter assembly 10 during the time period of the graph. The width of each spike is about 100 ms, wherein the 100 ms is the time it takes for an air bubble to pass through the meter assembly 10. The average frequency correlates to the average density of the fluid stream. The changes in frequency therefore can be related to the instantaneous density of the multiphase flow material stream.

Figure 16:
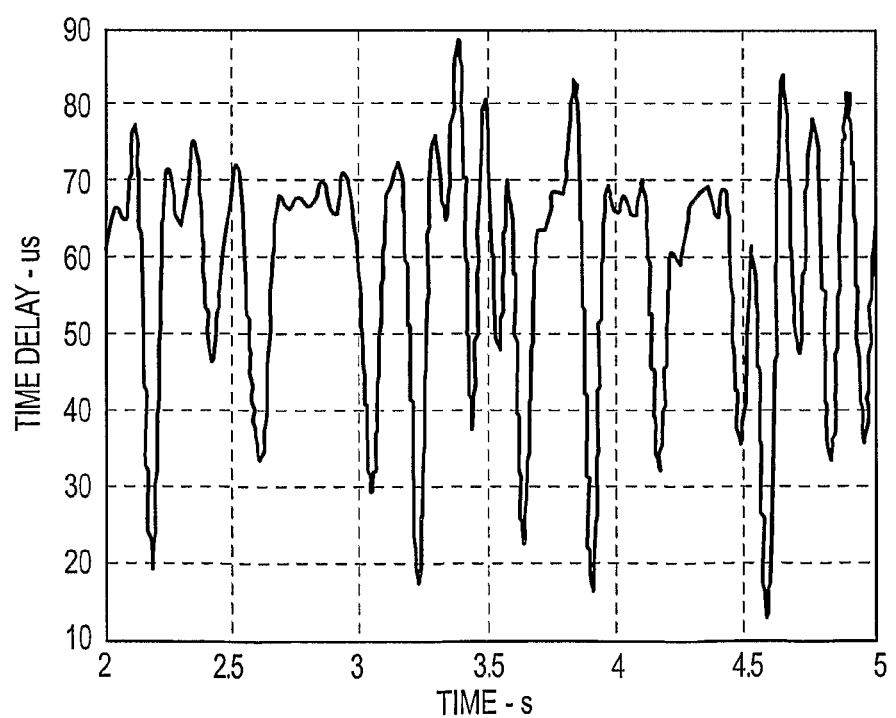
FIG. 16 is a graph of time delay versus time, wherein the downward spikes in the time delay flow characteristic again represent an anomaly in the flow material.

FIG. 16 is a graph of time delay versus time, wherein the downward spikes in the time delay flow characteristic again represent an anomaly in the flow material. The average time delay corresponds to the average mass flow of the fluid stream. Note the changes in time delay (i.e., a time delay decrease between the two sensors) as an air bubble passes through the meter assembly 10. The changes in time delay can be related to the instantaneous mass flow of the multi-phase flow stream, and can be used to detect an anomaly in the flow material.

Figure 17:
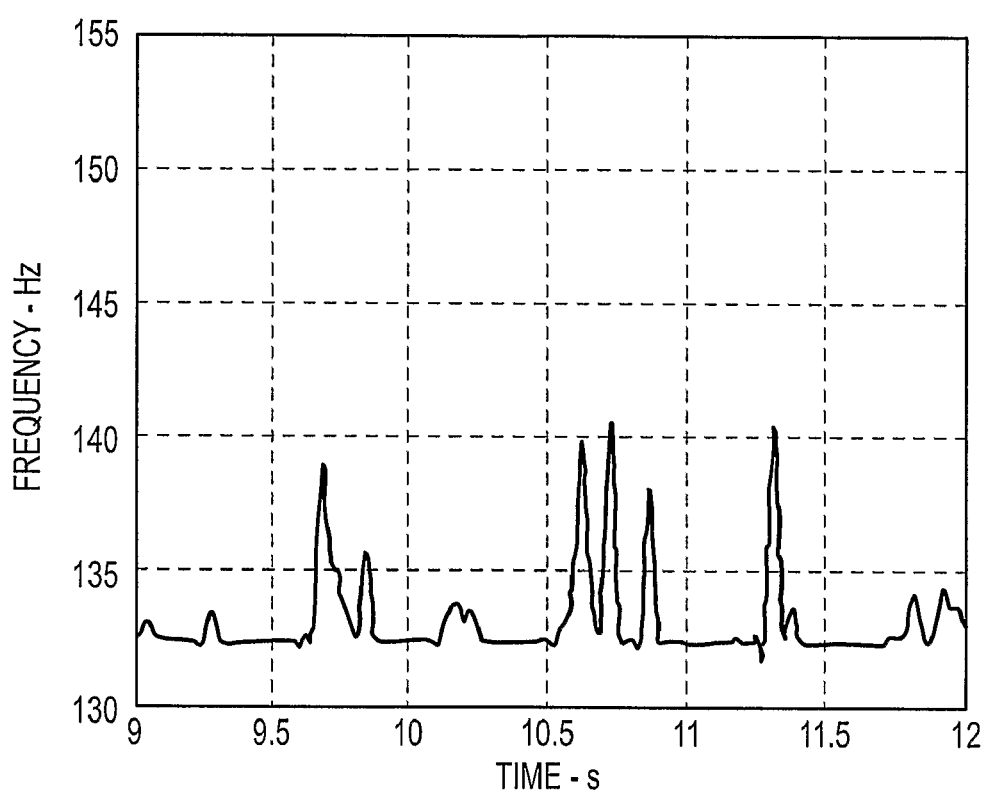
FIG. 17 shows frequency response versus time for a smaller void fraction of air in the flow material.

FIG. 17 shows frequency response versus time for a smaller void fraction of air in the flow material. Even though the void fraction is lower than in FIG. 15, the flow rate is the same and it still takes about 100 ms for an air bubble to pass through the meter assembly 10. From the graph, it can be seen that six air bubbles have passed through the meter assembly 10.

Figure 18:
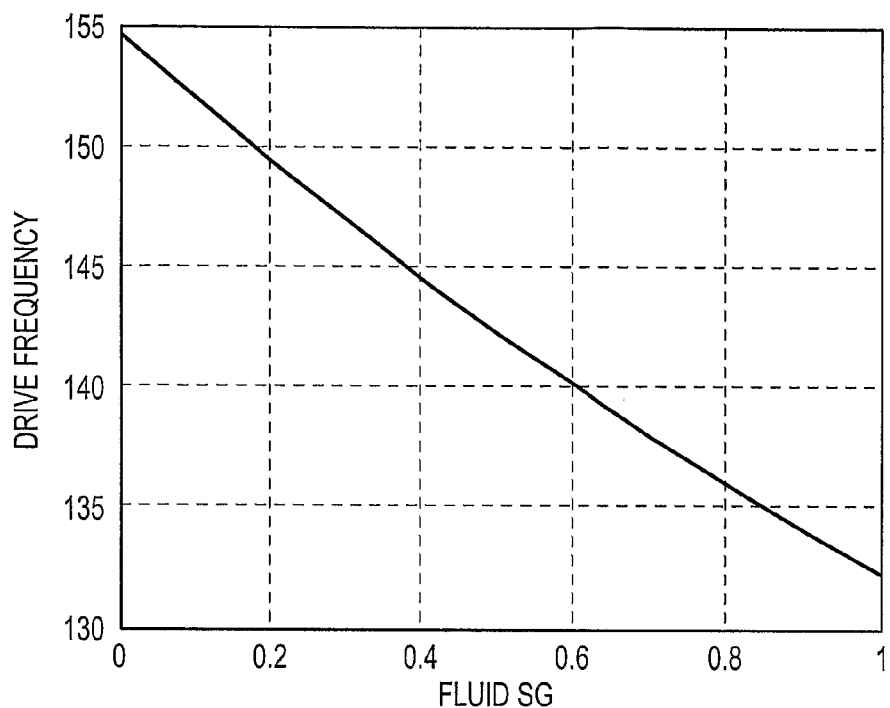
FIG. 18 is a graph of drive frequency versus fluid Specific Gravity (SG) for water plus entrained air.

FIG. 18 is a graph of drive frequency versus fluid Specific Gravity (SG) for water plus entrained air. In the graph, the value of SG for air is zero while water has a SG value of one. It can be seen from this figure that the Specific Gravity can be used to differentiate between the flow material and the anomalies in the flow material.

Figure 19:
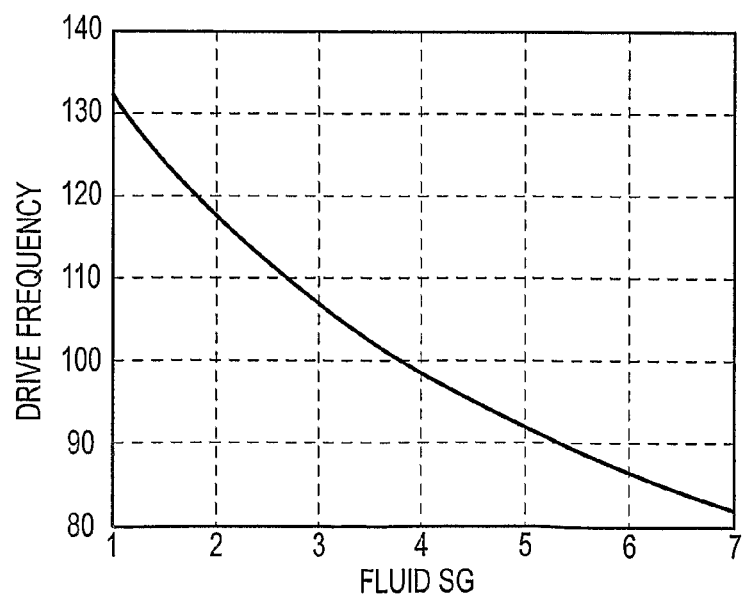
FIG. 19 is a graph of drive frequency versus SG for a SG range Of 1-7.

FIG. 19 is a graph of drive frequency versus SG for a SG range of 1-7. Solids have specific gravities greater than the SG of water (i.e., they have SG values of greater than 1). For example, steel has an SG of around 7. The drive frequency of a fluid with SG=7 is typically around 83 Hz. Therefore, when a solid with a different density than the flow material passes through the meter, a frequency change will occur that can be detected by the meter electronics 20. In the case of water as the flow material and steel as the anomaly material, the meter would operate at 132 Hz in the absence of an anomaly. The frequency flow characteristic will move downwards towards 83 Hz when a steel solid passes through the meter assembly 10.

The meter electronics 20 can subsequently set the anomaly condition 1412 that indicates the occurrence of the anomaly. The meter electronics 20 can subsequently set the anomaly alarm 1413 that can perform or initiate some manner of anomaly handling routine, process, or notification. The meter electronics 20 can subsequently increment the anomaly count 1414 that counts the detected anomaly conditions. The anomaly detection, indication, alarms, and count are discussed in more detail below in conjunction with the flowchart 2000 of FIG. 20.

It should be understood that the meter electronics 20 can iteratively receive and process the vibrational response. As a result, the meter electronics 20 can detect anomalies during operation of the associated flow meter. The meter electronics 20 can substantially continuously perform the anomaly indication, alarm, and count processes over time as various anomalies pass through the flow meter.

The vibrational response processing routine 1401 receives the vibrational response. As previously discussed, the vibrational response can include first and second sensor signals that reflect the response of the one or more flow conduits to a drive vibration imposed on the flow meter. The vibrational response processing routine 1401 in some embodiments processes the vibrational response in order to obtain one or more flow characteristics of the flow material. The one or more flow characteristics can include a frequency response, a phase difference between the first and second sensor signals, a density, a mass flow rate, a volume flow rate, etc. The frequency response is inherently related to the flow of flow material through the flow meter (as are all of the derived flow characteristics). The frequency therefore varies with the mass flow rate in the flow meter. The frequency also varies with the density of the flow material. For example, where the flow material comprises a liquid, entrained gas passing through the flow meter will cause the frequency to momentarily spike up to a higher frequency value, as the mass in the flow meter drops and as the vibrational response is temporarily less damped by flow material. Therefore, by employing the fast frequency and phase difference determinations, the meter electronics 20 can detect anomalies in the flow, and can substantially instantaneously detect the anomalies. In addition, the meter electronics 20 in some embodiments and under some flow conditions can quantify the anomalies.

The anomaly detect routine 1402 in one embodiment compares the vibrational response to at least one anomaly profile 1411 (discussed below). If the vibrational response falls within the anomaly profile 1411, then the anomaly detect routine 1402 determines that an anomaly is occurring.

The anomaly indicate routine 1403 in one embodiment sets an anomaly condition 1412 (discussed below). The anomaly indicate routine 1403 therefore indicates the occurrence of the anomaly. In one embodiment, the anomaly indicate routine 1403 increments the anomaly count 1414.

The anomaly alarm routine 1404 in one embodiment sets the anomaly alarm 1413. The anomaly alarm 1413 can perform or initiate any manner of anomaly handling routine, process, or notification.

The vibrational response 1410 stores a vibrational response received from the meter assembly 10. The vibrational response 1410 can comprise any manner of data storage, such as a circular queue, for example. The vibrational response 1410 can comprise digital representations of an analog electrical signal received from the meter assembly 10. The vibrational response 1410 can comprise sampled portions of the electrical signal. The vibrational response 1410 can include first and second sensor signals and can further include flow characteristics derived from the first and second sensor signals. For example, the vibrational response 1410 can include a frequency value (i.e., a frequency approximation or estimation) that is derived from the first and second sensor signals.

The anomaly profile 1411 stores one or more profiles that are used in order to detect anomalies in the flow material. Multiple anomaly profiles can be included where multiple anomaly types are desired to be detected. A stored anomaly profile can include any information that enables an anomaly determination.

In one embodiment, the anomaly profile can include an anomaly frequency profile. The anomaly frequency profile can comprise a frequency threshold that is above or below an expected flow material frequency characteristic. When the vibrational response exceeds the anomaly frequency threshold, then an anomaly occurrence is determined to exist. Alternatively, in another embodiment, the anomaly frequency profile can comprise a frequency range. The anomaly frequency range can comprise a frequency range that is above or below the associated flow characteristic. When the vibrational response is within the anomaly frequency range, then an anomaly occurrence is determined to exist. The anomaly frequency range can be specific to the phase and composition of the anomalous material. For example, the anomaly frequency range can be specific to a particular gas, such as natural gas in a crude oil flow stream, and the meter electronics 20 therefore can detect natural gas bubbles in the crude oil.

In one embodiment, the anomaly profile can include an anomaly amplitude profile. The anomaly amplitude profile can include an anomaly amplitude threshold or an anomaly amplitude range. The anomaly amplitude threshold/range can comprise a density, mass flow rate, or time or phase delay amplitude value, for example. However, the anomaly amplitude threshold/range can include other flow characteristics. The anomaly amplitude threshold/range can be above or below an expected flow material flow characteristic. When the vibrational response exceeds or falls within the anomaly amplitude threshold/range, then an anomaly occurrence is determined to exist.

In one embodiment, the anomaly profile can include a time duration profile. The time duration profile can comprise a time duration of a deviation from the expected flow material characteristic. For example, a typical air bubble in water will transit through the meter assembly 10 in about 100 milliseconds (ms). If a frequency response includes a frequency spike that is about 100 ms in duration, the time duration profile alone may be used in order to make an air bubble anomaly determination. As a result, when an associated flow characteristic deviates from the expected flow material frequency characteristic for a time period that falls within the time duration profile, then an anomaly occurrence is determined to exist.

In one embodiment, the anomaly profile can include one or more of the above frequency, amplitude, and time duration thresholds/ranges. For example, for air bubble detection, the anomaly profile 1411 can comprise both a frequency threshold/range and an anomaly time duration profile. Other combinations can be used, depending on the anomalous material or materials to be detected. The detection in one embodiment employs pattern recognition.

The anomaly condition 1412 can comprise a state variable that indicates whether an anomaly is currently occurring. For example, because the meter electronics 20 can quickly or substantially instantaneously determine flow characteristics, the anomaly condition 1412 can indicate an anomaly in substantially real time. In one example, the anomaly condition 1412 can be set to a TRUE or ON value while an air bubble is passing through the meter assembly 10, and can be set to FALSE otherwise.

The anomaly alarm 1413 can comprise a state variable that indicates an alarm condition. The anomaly alarm 1413 can be set to TRUE when an anomaly is determined to be occurring. The anomaly alarm 1413 can be used to initiate some manner of routine, processing, or notification to be performed during the anomaly. For example, if a solid is detected in the flow material, the anomaly alarm 1413 can initiate an anomaly display to an operator, can initiate an anomaly message to another device, etc.

The anomaly count 1414 can be used to count anomaly occurrences. The anomaly count 1414 can count gas or air bubbles, pockets of foreign liquids, or solids in the flow material. The anomaly count 1414 can be incremented at every detection of an anomaly. The anomaly count 1414 can be incremented when the anomaly condition 1412 is set to a TRUE state, for example.

Figure 20:
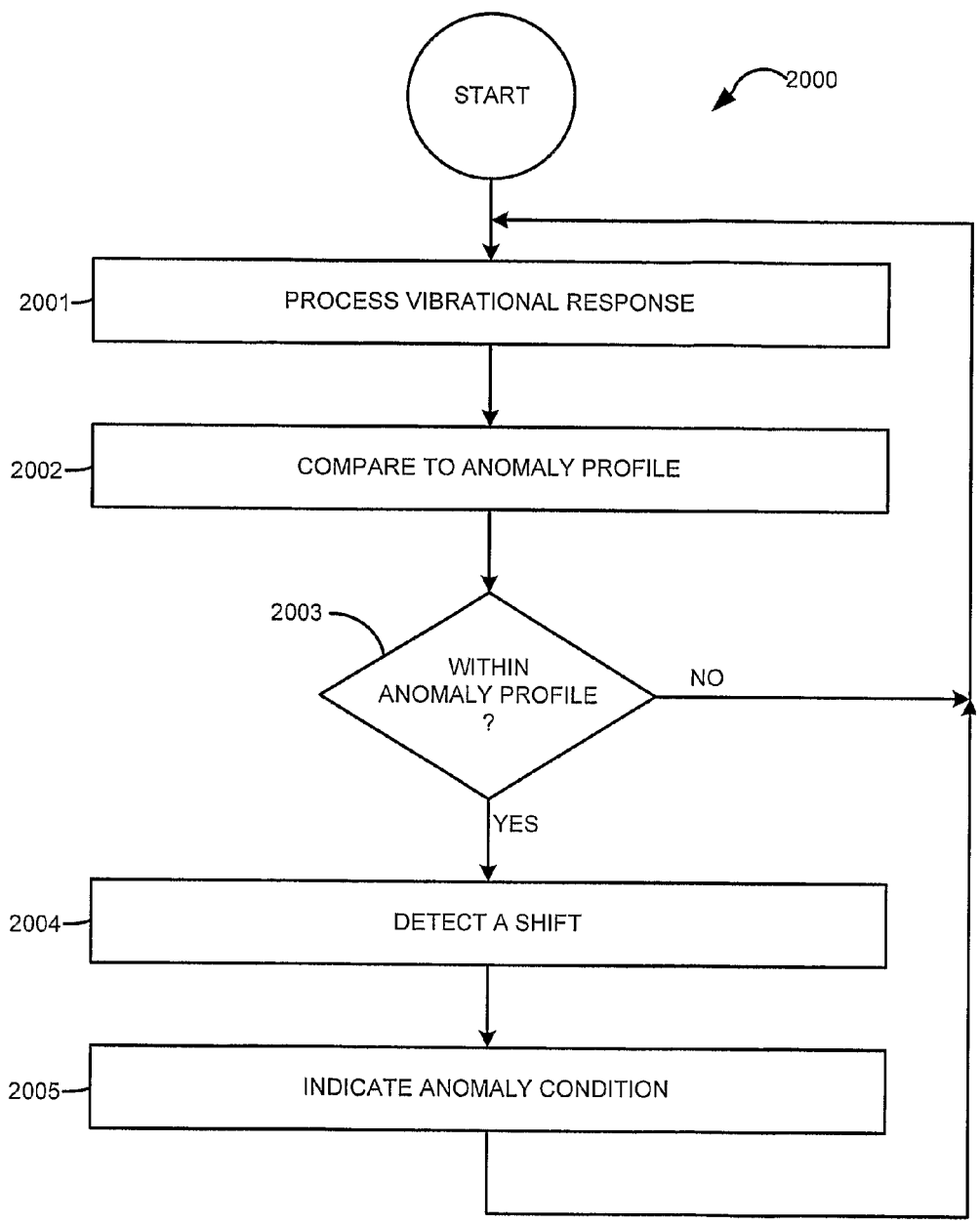
FIG. 20 is a flowchart of a method for detecting a flow anomaly in a flow material flowing through a flow meter according to an embodiment of the invention.

FIG. 20 is a flowchart 2000 of a method for detecting a flow anomaly in a flow material flowing through a flow meter according to an embodiment of the invention. In step 2001, a vibrational response is processed. The vibrational response can be processed in order to determine one or more flow characteristics. The vibrational response can comprise a first and second sensor signals, for example. The one or more flow characteristics can include a frequency of the vibrational response, a phase difference between the first and second sensor signals comprising the vibrational response, a density, a mass flow rate, a volume flow rate, a time delay, etc.

In step 2002, the vibrational response is compared to an anomaly profile. As previously discussed, the anomaly profile can provide information that enables detection of an anomaly of many different types. The anomaly profile can specify a gas anomaly to be detected. The anomaly profile can specify a foreign liquid anomaly to be detected. The anomaly profile can specify a solid anomaly to be detected.

The anomaly profile can include an amplitude profile, such as an amplitude anomaly threshold or an amplitude anomaly range. The amplitude profile can comprise a profile of a frequency, density, or mass flow rate flow characteristic.

The anomaly profile can include a frequency profile, such as a frequency anomaly threshold or frequency anomaly range that can be used to determine an anomaly in the flow material.

The anomaly profile can include a time duration profile. The time duration profile can indicate an anomaly if the vibrational response deviates from an expected response according to the time duration profile.

The anomaly profile can comprise a bubble profile, including an air bubble profile. The bubble profile can specify any combination of amplitude, frequency, and/or time values that indicate an anomaly in the flow material. For example, the bubble profile in one embodiment can include a frequency threshold of frequencies above 135 Hz and a time duration of about 100 ms, where the flow material is water and the bubble comprises an air bubble. However, other frequency thresholds and time durations are contemplated and are within the scope of the description and claims.

It should be understood that the anomaly profile can include one or more of the above factors. The anomaly profile can be selected or created for a predetermined flow material and for one or more predetermined anomaly types that are expected in the flow material.

In step 2003, if the vibrational response is within the anomaly profile, then the method proceeds to step 2004; otherwise, the method branches around steps 2004 and 2005.

In step 2004, because the vibrational response falls within the anomaly profile, then a shift in the vibrational response is detected.

In step 2005, because the shift has occurred, an anomaly is indicated. As previously discussed, the indication can include multiple actions. In one embodiment, the anomaly condition 1412 can be set to a TRUE state as long as the anomaly is detected. For an air bubble in a water flow material, an air bubble will typically take about 100 ms to pass through the flow meter. In one embodiment, the anomaly alarm 1413 can be set to TRUE, wherein the alarm state can perform or initiate some manner of anomaly handling routine, process, or notification. In one embodiment, an anomaly count 1414 can be incremented, wherein the anomaly count 1414 counts occurrences of anomalies in the flow condition. For example, the anomaly count 1414 can count occurrences of gas bubbles, air bubbles, or solids in the flow material.

It should be understood that the above method steps can be iteratively performed. As the vibrational response is continuously received, it can be iteratively processed and compared, and anomalies in the flow material can be substantially continuously detected and indicated. Any anomalies can be detected and indicated substantially in real time. The flowchart therefore loops back to step 2001.

The meter electronics and method according to the invention can be employed according to any of the embodiments in order to provide several advantages, if desired. Advantageously, by employing the fast frequency and phase determinations, the meter electronics can detect anomalies in the flow. The invention can quickly and accurately detect a flow anomaly. The invention can detect anomalies substantially instantaneously. The invention in some embodiments and under some flow conditions can quantify the anomalies.

The invention can detect a gas bubble in the flow material. The invention can detect an air bubble in the flow material. The invention can count air bubbles in the flow material. The invention can determine bubble boundaries of bubbles in the flow material. The invention can detect foreign liquids in the flow material. The invention can detect solids in the flow material. The invention can count solids in the flow material.

We claim:

1. Meter electronics (20) for detecting a flow anomaly in a flow material flowing through a flow meter (5), the meter electronics (20) comprising:
   an interface (201) for receiving a vibrational response of the flow material, with the vibrational response including at least a first sensor signal and a second sensor signal; and
   a processing system (203) in communication with the interface (201) and configured to receive the vibrational response from the interface (201), generate a ninety degree phase shift from the first sensor signal and generate at least a frequency using the first sensor signal and the ninety degree phase shift, compare the frequency to at least one anomaly profile, detect a flow anomaly occurrence if the frequency falls within an anomaly profile, and indicate an anomaly condition as a result of the detecting.

2. The meter electronics (20) of claim 1, with the interface (201) including a digitizer configured to digitize the sensor signal.

3. The meter electronics (20) of claim 1, wherein the processing system (203) is further configured to iteratively perform the receiving, generating, comparing, detecting, and indicating.

4. The meter electronics (20) of claim 1, with the flow meter (5) comprising a Coriolis flow meter.

5. The meter electronics (20) of claim 1, with the flow meter (5) comprising a vibrating densitometer.

6. The meter electronics (20) of claim 1, wherein the processing system (203) is further configured to compute a phase difference response using the ninety degree phase shift, the first sensor signal, and the second sensor signal.

7. The meter electronics (20) of claim 1, wherein the processing system (203) is further configured to generate a second ninety degree phase shift from the second sensor signal and compute a phase difference response using the ninety degree phase shift, the second ninety degree phase shift, the first sensor signal, and the second sensor signal.

8. The meter electronics (20) of claim 1, further comprising generating a sensor signal time delay response.

9. The meter electronics (20) of claim 1, further comprising generating a mass flow rate response.

10. The meter electronics (20) of claim 1, farther comprising generating a density response.

11. The meter electronics (20) of claim 1, with the indicating comprising indicating a solids anomaly.

12. The meter electronics (20) of claim 1, with the indicating comprising indicating a foreign liquid anomaly.

13. The meter electronics (20) of claim 1, with the indicating comprising indicating a gas anomaly.

14. The meter electronics (20) of claim 1, with the indicating comprising indicating an air bubble anomaly.

15. The meter electronics (20) of claim 1, with the indicating comprising setting an anomaly alarm condition.

16. The meter electronics (20) of claim 1, with the indicating comprising incrementing an anomaly count.

17. A method for detecting a flow anomaly in a flow material flowing through a flow meter, the method comprising:
   receiving a vibrational response from the flow meter, with the vibrational response including at least a first sensor signal and a second sensor signal;
   generating a ninety degree phase shift from the first sensor signal and generating at least a frequency using the first sensor signal and the ninety degree phase shift;
   comparing the frequency to at least one anomaly profile;
   detecting a flow anomaly occurrence if the frequency falls within the anomaly profile; and
   indicating an anomaly condition as a result of the detecting.

18. The method of claim 17, further comprising iteratively performing the receiving, generating, comparing, detecting, and indicating.

19. The method of claim 17, with the flow meter comprising a Coriolis flow meter.

20. The method of claim 17, with the flow meter comprising a vibrating densitometer.

21. The method of claim 17, further comprising computing a phase difference response using the ninety degree phase shift, the first sensor signal, and the second sensor signal.

22. The method of claim 17, further comprising:
   generating a second ninety degree phase shift from the second sensor signal; and
   computing a phase difference response using the ninety degree phase shift, the second ninety degree phase shift, the first sensor signal, and the second sensor signal.

23. The method of claim 17, further comprising generating a sensor signal time delay response.

24. The method of claim 17, further comprising generating a mass flow rate response.

25. The method of claim 17, further comprising generating a density response.

26. The method of claim 17, with the indicating comprising indicating a solids anomaly.

27. The method of claim 17, with the indicating comprising indicating a foreign liquid anomaly.

28. The method of claim 17, with the indicating comprising indicating a gas anomaly.

29. The method of claim 17, with the indicating comprising indicating an air bubble anomaly.

30. The method of claim 17, with the indicating comprising setting an anomaly alarm condition.

31. The method of claim 17, with the indicating comprising incrementing an anomaly count.

32. A method for detecting a flow anomaly in a flow material flowing through a flow meter, the method comprising:
   receiving a vibrational response from the flow meter, with the vibrational response including at least a first sensor signal and a second sensor signal;
   generating a ninety degree phase shift from the first sensor signal and generating at least a frequency using the first sensor signal and the ninety degree phase shift;

comparing the frequency to at least a gas anomaly profile;
detecting a flow anomaly occurrence if the frequency falls within the gas anomaly profile; and
incrementing a bubble count as a result of the detecting.

33. The method of claim 32, further comprising iteratively performing the receiving, generating, comparing, detecting, and incrementing.

34. The method of claim 32, with the flow meter comprising a Coriolis flow meter.

35. The method of claim 32, with the flow meter comprising a vibrating densitometer.

36. The method of claim 32, further comprising computing a phase difference response using the ninety degree phase shift, the first sensor signal, and the second sensor signal.

37. The method of claim 32, further comprising:
generating a second ninety degree phase shift from the second sensor signal; and
computing a phase difference response using the ninety degree phase shift, the second ninety degree phase shift, the first sensor signal, and the second sensor signal.

38. The method of claim 32, further comprising generating a sensor signal time delay response.

39. The method of claim 32, further comprising generating a mass flow rate response.

40. The method of claim 32, further comprising generating a density response.

41. The method of claim 32, further comprising setting an anomaly alarm condition.

42. The method of claim 32, further comprising incrementing an anomaly count.

* * * * *

UNITED STATES PATENT AND TRADEMARK OFFICE
CERTIFICATE OF CORRECTION

PATENT NO. : 7,908,097 B2  Page 1 of 1
APPLICATION NO. : 11/914819
DATED : March 15, 2011
INVENTOR(S) : Graeme Ralph Duffill et al.

It is certified that error appears in the above-identified patent and that said Letters Patent is hereby corrected as shown below:

Column 17, Line 12 and Line 13, replace equation (34) with $$\phi = \tan^{-1}\left[\frac{\sin\phi}{\cos\phi}\right] \quad (34)$$ --

Signed and Sealed this
Ninth Day of August, 2011

David J. Kappos
*Director of the United States Patent and Trademark Office*